(12) United States Patent
Hwang et al.

(10) Patent No.: US 11,279,943 B2
(45) Date of Patent: Mar. 22, 2022

(54) RECOMBINANT VECTOR FOR EXPRESSING TARGET PROTEIN IN PLANT CELL

(71) Applicant: BIOAPPLICATIONS INC., Pohang-si (KR)

(72) Inventors: In Hwan Hwang, Pohang-si (KR); Hyang Ju Kang, Pohang-si (KR)

(73) Assignee: BIOAPPLICATIONS INC., Pohang-si (KR)

( * ) Notice: Subject to any disclaimer, the term of this patent is extended or adjusted under 35 U.S.C. 154(b) by 0 days.

(21) Appl. No.: 16/478,592

(22) PCT Filed: Jan. 17, 2018

(86) PCT No.: PCT/KR2018/000807
§ 371 (c)(1),
(2) Date: Jul. 17, 2019

(87) PCT Pub. No.: WO2018/135860
PCT Pub. Date: Jul. 26, 2018

(65) Prior Publication Data
US 2020/0354737 A1 Nov. 12, 2020

(30) Foreign Application Priority Data

Jan. 17, 2017 (KR) .................. 10-2017-0008160

(51) Int. Cl.
| | | |
|---|---|---|
| *C12P 21/04* | (2006.01) | |
| *C12P 21/06* | (2006.01) | |
| *C12N 5/00* | (2006.01) | |
| *C12N 5/02* | (2006.01) | |
| *A61K 38/16* | (2006.01) | |
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C12N 15/82* | (2006.01) | |
| *C07K 14/705* | (2006.01) | |
| *C12P 21/00* | (2006.01) | |
| *C07K 14/435* | (2006.01) | |
| *A61K 38/17* | (2006.01) | |

(52) U.S. Cl.
CPC .......... *C12N 15/8257* (2013.01); *A61K 38/17* (2013.01); *C07K 14/435* (2013.01); *C07K 14/70589* (2013.01); *C12P 21/005* (2013.01); *C07K 2319/04* (2013.01); *C07K 2319/31* (2013.01); *C07K 2319/75* (2013.01); *C07K 2319/91* (2013.01)

(58) Field of Classification Search
None
See application file for complete search history.

(56) References Cited

U.S. PATENT DOCUMENTS

| | | | | |
|---|---|---|---|---|
| 2007/0161081 A1* | 7/2007 | Jin | ............................ | A61P 1/00 |
| | | | | 435/69.1 |
| 2007/0161087 A1* | 7/2007 | Glaesner | ................ | C12N 15/62 |
| | | | | 435/69.7 |
| 2020/0354726 A1* | 11/2020 | Hwang | .............. | C12N 15/8257 |

FOREIGN PATENT DOCUMENTS

| | | |
|---|---|---|
| JP | 2006-176504 A | 7/2006 |
| JP | 2009-515520 A | 4/2009 |
| KR | 10-1449155 B1 | 10/2014 |

OTHER PUBLICATIONS

Xue et al. Regulation of galectin-3-induced apoptosis of Jurkat cells by both O-glycans and N-glycans on CD45. (2013) FEBS Letters; vol. 587; pp. 3986-3994 (Year: 2013).*
Castilho et al., N-glycosylation engineering of plants for the biosynthesis of glycoproteins with bisected and branched complex N-glycans, Glycobiology, 2011, vol. 21(6), pp. 813-823.
Lee et al., Oral immunization of haemaggulutinin H5 expressed in plant endoplasmic reticulum with adjuvant saponin protects mice against highly pathogenic avian influenza A virus infection, Plant Biotechnology Journal, 2015, vol. 13, pp. 62-72.
NCBI, GenBank accession No. AAS46946.1 (Jul. 26, 2016).
Okamoto et al., "Enhanced expression of an antimicrobial peptide sarcotoxin IA by GUS fusion in transgenic tobacco plants", Plant and Cell Physiology, 1998, vol. 39(1), pp. 57-63.
Sagt et al., "Introduction of an N-glycosylation site increases secretion of heterologous proteins in yeasts", Applied and Environmental Microbiology, 2000, vol. 66(11), pp. 4940-4944.
Symons et al., "Domain organization of the extracellular region of CD45", Protein Engineering, 1999, vol. 12(10), pp. 885-892.
Xu et al., "Enhanced accumulation of secreted human growth hormone by transgenic tobacco cells correlates with the introduction of an N-glycosylation site", Journal of Biotechnology, 2011, vol. 154, pp. 54-59.
Japanese Office Action for corresponding Japanese Application No. 2019-538440, dated Jul. 31, 2020, 15 pages.
Japanese Decision for Refusal for corresponding Japanese Application No. 2019-538440, dated Mar. 16, 2021, 11 pages.

* cited by examiner

*Primary Examiner* — Thea D' Ambrosio
(74) *Attorney, Agent, or Firm* — Vorys, Sater, Seymour & Pease LLP; Mih Suhn Koh

(57) ABSTRACT

Provided is a technique for highly expressing a target protein in a plant cell by using a glycosylation domain, a recombinant vector comprising a gene encoding a fusion protein of a glycosylation domain and a target protein, a recombinant cell, a transformed plant, and a method of producing a target protein using these.

14 Claims, 15 Drawing Sheets
Specification includes a Sequence Listing.

FIG. 1

BiP:Leptin:M Recombinant vector information

| p35S | M17 | BiP | Leptin | M | HA | HDEL | HSPt |

Enk furin

XbaI    BamHI    SpeI    XhoI tctagaggcttgtgtgtgtaaagaatggctcggccccgttttggagctaacagtaccgtgtgttggatcatctctcgtcgag
tgattttccgatcatctcggattaagatctagtgtgctaatcatgttgcttcagcacctttctcttcgttcctgattctaag
tgttttcttcgaatttacgaactaaaagttact

RECOMBINANT VECTOR FOR EXPRESSING TARGET PROTEIN IN PLANT CELL

CROSS-REFERENCE TO RELATED APPLICATION

This application is a 371 of PCT/KR2018/0000807, filed Jan. 17, 2018, which claims the benefit of priority from Korean Patent Application No. 10-2017-0008160, filed Jan. 17, 2017, the contents of each of which are incorporated herein by reference in its entirety.

SEQUENCE LISTING

The Sequence Listing submitted in text format (.txt) filed on Jul. 30, 2021, named "SequenceListing.txt", created on Jul. 30, 2021 (28.2 KB), is incorporated herein by reference.

TECHNICAL FIELD

The present invention relates to a technique for highly expressing a target protein in a plant cell by using a glycosylation domain, a recombinant vector comprising a gene encoding a fusion protein of a glycosylation domain and a target protein, a recombinant cell, a transgenic plant, and a method of producing a target protein using these.

BACKGROUND ART

The remarkable development of molecular biology and genetic engineering techniques has also been applied to the plant field, and efforts to produce useful physiologically active substances from plants are steadily continuing. When producing useful substances in plants, production costs may be dramatically reduced, various contaminants such as viruses, oncogenes, and enterotoxins that may be generated in a conventional method of separating and purifying a protein through synthesis in animal cells or microorganisms may be fundamentally excluded, and unlike animal cells or microorganisms, such useful substances may be stored and managed as seeds for a long period of time even in the commercialization stage. In addition, when demand for the corresponding useful substance surges, the above system is absolutely advantageous compared to existing animal cell systems in terms of equipment technology or costs required for mass production, and thus supply corresponding to the increased demand is possible within the shortest time.

Despite these advantages, however, a relatively low level of protein expression is the biggest drawback in protein production in plant cells, compared to other hosts including animal cells. Thus, many studies have been conducted and there have been attempts to increase a protein expression level in plant cells by using various methods.

Previous studies to increase a level of target protein expression in a plant cell have been focused mainly on a transcription stage prior to a translation stage where a protein is produced from mRNA during a protein expression process, and few studies have been conducted on a method of increasing a protein expression level when a protein is translated from mRNA.

Meanwhile, it is well known that conventional N-glycosylation affects protein stability. In this case, N-glycans were thought to enhance stability because they protect proteins from proteases. It is also known that other mechanisms provide an additional binding force for protein three-dimensional structures to thereby provide stability.

As a result of having made intensive efforts to increase an expression level of a target protein in the translation stage in producing a target protein in a plant cell, the inventors of the present invention confirmed that, when a small domain causing glycosylation is fused to a target protein, an expression level of the protein was increased, and verified that production efficiency of the target protein could be increased in a transgenic plant by using the above finding, thus completing the present invention.

DISCLOSURE

Technical Problem

The present invention relates to a use of an N-glycosylation domain in target protein expression.

An embodiment provides a composition for expressing a target protein, which comprises one or more selected from the group consisting of a gene encoding an N-glycosylation domain, a recombinant vector comprising the gene, and a recombinant cell comprising the recombinant vector.

The composition for expressing a target protein may further comprise a gene encoding the target protein or a recombinant vector comprising the gene. In this regard, the gene encoding the target protein and the gene encoding an N-glycosylation domain may be comprised in the form of a gene encoding a fusion protein comprising the N-glycosylation domain and the target protein or a recombinant vector comprising the gene.

The N-glycosylation domain may be an N-glycosylation domain (e.g., multiple N-glycosylation domains) comprising one or more N-glycosylation sites or two or more N-glycosylation sites. In one embodiment, the N-glycosylation domain may comprise a CD45-derived M domain, such as a human CD45-derived M domain or a portion thereof. The target protein expression may be performed in a eukaryotic cell (e.g., a plant cell) or a eukaryotic organism (e.g., a plant).

Another embodiment provides a recombinant vector comprising a gene encoding a fusion protein comprising an N-glycosylation domain and a target protein.

Another embodiment provides a recombinant cell into which the recombinant vector is introduced. The recombinant cell may be a eukaryotic cell, for example, a plant cell.

The recombinant vector comprising a gene encoding a fusion protein and/or the recombinant cell may be used for enhancing production of the target protein. Therefore, another embodiment provides a composition for producing a target protein or enhancing production of a target protein, which comprises a recombinant vector comprising a gene encoding a fusion protein comprising an N-glycosylation domain and a target protein and/or a recombinant cell.

Another embodiment provides a transgenic organism into which the recombinant vector comprising a gene encoding a fusion protein comprising an N-glycosylation domain and a target protein is introduced. The transgenic organism may be a transgenic eukaryotic organism, for example, a transgenic plant.

Another embodiment provides a method of producing a target protein or enhancing production of a target protein, comprising introducing, into a cell, the composition for producing a target protein or enhancing production of a target protein. The method may increase an expression level or productivity of the target protein, compared to a case in which a gene encoding the target protein is introduced alone into a cell (i.e., introduced via an N-glycosylation domain-free recombinant vector).

Technical Solution

The present invention has been made to address the above-described problems, and provides a use of an N-glycosylation domain for expressing a target protein in a plant, more particularly, a technique for increasing an expression level of a target protein by expressing a fusion gene produced by fusing a gene encoding the target protein and a gene encoding an N-glycosylation domain to a C-terminal-corresponding site (3'-terminal) or N-terminal-corresponding site (5'-terminal) of the gene.

An embodiment provides a composition for expressing a target protein, which comprises one or more selected from the group consisting of a gene encoding an N-glycosylation domain, a recombinant vector comprising the gene, and a recombinant cell comprising the recombinant vector.

The composition for expressing a target protein may further comprise a gene encoding the target protein or a recombinant vector comprising the gene. In this regard, the gene encoding the target protein and the gene encoding an N-glycosylation domain may be comprised in the form of a gene encoding a fusion protein comprising the N-glycosylation domain and the target protein or a recombinant vector comprising the gene.

The N-glycosylation domain may be an N-glycosylation domain comprising one or more N-glycosylation sites or two or more N-glycosylation sites. In one embodiment, the N-glycosylation domain may comprise a CD45-derived M domain or a portion thereof, for example, a human CD45-derived M domain or a portion thereof. The target protein expression may be performed in a eukaryotic cell (e.g., a plant cell) or a eukaryotic organism (e.g., a plant).

Another embodiment provides a recombinant vector comprising a gene encoding a fusion protein comprising an N-glycosylation domain and a target protein. The recombinant vector may be used for expression in a eukaryotic cell, for example, a plant cell.

Another embodiment provides a recombinant cell comprising the gene encoding a fusion protein comprising an N-glycosylation domain and a target protein. The recombinant cell may be a cell into which a recombinant vector comprising a gene encoding a fusion protein comprising an N-glycosylation domain and a target protein is introduced. The cell may be a eukaryotic cell, for example, a plant cell.

Another embodiment provides a transgenic organism comprising the gene encoding a fusion protein comprising an N-glycosylation domain and a target protein. The transgenic organism may be an organism into which a recombinant vector comprising a gene encoding a fusion protein comprising an N-glycosylation domain and a target protein is introduced. The transgenic organism may be a transgenic eukaryotic organism, for example, a transgenic plant. The transgenic organism may be a eukaryotic organism (e.g., a plant) comprising the above-described recombinant cell.

The recombinant vector comprising a gene encoding a fusion protein and/or the recombinant cell and/or the transgenic organism may be used for producing a target protein or enhancing the production of a target protein.

Therefore, another embodiment provides a composition for producing a target protein or enhancing the production of a target protein, the composition comprising one or more selected from the group consisting of a gene encoding a fusion protein comprising an N-glycosylation domain and a target protein, a recombinant vector comprising the gene, a recombinant cell comprising the recombinant vector, and a transgenic organism comprising the recombinant vector.

Another embodiment provides a method of producing a target protein or enhancing the production of a target protein, comprising culturing a recombinant cell comprising a gene encoding a fusion protein comprising an N-glycosylation domain and a target protein. The recombinant cell may be a cell into which a recombinant vector comprising a gene encoding a fusion protein comprising an N-glycosylation domain and a target protein is introduced. The cell may be a eukaryotic cell, for example, a plant cell. The method may further comprise, before the culturing process, introducing, into a cell, a recombinant vector comprising a gene encoding a fusion protein comprising an N-glycosylation domain and a target protein. The method may further comprise, after the culturing process, isolating (or extracting) and/or purifying a target protein from the cultured cell (a cell, cell debris, or a cell lysate) and/or a culture medium.

Another embodiment provides a method of producing a target protein or enhancing the production of a target protein, comprising growing a transgenic organism comprising a gene encoding a fusion protein comprising an N-glycosylation domain and a target protein. The organism may be a eukaryotic organism, for example, a plant. The method may further comprise, before the growing process, introducing, into an organism, a recombinant vector comprising a gene encoding a fusion protein comprising an N-glycosylation domain and a target protein. The method may further comprise, after the growing process, isolating (or extracting) and/or purifying a target protein from the eukaryotic organism (e.g., a plant), or a cell of the eukaryotic organism (a cell, cell debris, cell lysate or a culture of the cell).

The method may increase an expression level or productivity of the target protein, compared to a case in which a gene encoding the target protein is introduced alone into a cell or an organism (i.e., introduced via an N-glycosylation domain-free recombinant vector), a case in which a target protein fused with an O-glycosylation domain is used, and/or a case in which the target protein intrinsically contains an N-glycosylation site without being fused with a separate N-glycosylation domain.

In one embodiment, the N-glycosylation domain may be a polypeptide having one or more N-glycosylation sites or two or more N-glycosylation sites (N-glycosylated amino acid; asparagine (Asn)), for example, 1, 2, 3, 4, 5, 6, 7, 8, 9, or 10 N-glycosylation sites and having a total number of amino acids of 10 to 100 or 20 to 80. In one embodiment, the N-glycosylation domain may be a polypeptide comprising 10 to 100 or 20 to 80 consecutive amino acids comprising at least a human CD45-derived M domain (having 4 N-glycosylation sites) in human CD45 or a portion thereof. For example, the human CD45 protein may have an amino acid sequence represented by SEQ ID NO: 5 (UniProt No. P08575). The human CD45-derived M domain may be a polypeptide consisting of a total of 60 amino acids from Ala (residue 231) to Asp (residue 290) of the human CD45 protein (SEQ ID NO: 5) (60aa; A<u>N</u>ITVDYLYN KETKLFTAKL NVNENVECG<u>N</u> NTCTNNEVH<u>N</u> LTECK <u>N</u>ASVS ISHNSCTAPD; SEQ ID NO: 2; underlined and bold characters denote N-glycosylation sites). In one embodiment, a gene encoding the human CD45-derived M domain may comprise a nucleic acid sequence of SEQ ID NO: 1. A portion of the human CD45-derived M domain may be a fragment of a polypeptide comprising 10 or more, 15 or more, or 20 or more consecutive amino acids having one or more N-glycosylation sites or two or more N-glycosylation sites, for example, 1, 2, 3, or 4 N-glycosylation sites in the CD45-derived M domain (e.g., selected from N(Asn) at residue 2, N(Asn) at residue 30, N(Asn) at residue 40, and N(Asn) at residue 46 of SEQ ID NO: 2). The fragment of the polypeptide may be a polypeptide comprising 10 or more, 15 or more, or 20 or more consecutive amino acids having one or more amino acid residue selected from N at residue 40 and N at residue 46 of the amino acid sequence of SEQ ID NO: 2, and may be, for example, "LTECKNASVS ISHN-SCTAPD (SEQ ID NO: 6)" or "NVNENVECGN NTCTN-NEVHN LTECKNASVS ISHNSCTAPD (SEQ ID NO: 7)", but the present invention is not limited thereto. In one embodiment, the N-glycosylation domain may be a polypeptide (e.g., SEQ ID NO: 6, 7, or 8) comprising 10 to 100 or 20 to 80 consecutive amino acids having an M domain (SEQ ID NO: 2) or an M domain portion comprising 10 or more, 15 or more, or 20 consecutive amino acids of the M domain (SEQ ID NO: 2), in the human CD45 protein (SEQ ID NO: 5). In one embodiment, a gene encoding the M domain may have a nucleic acid sequence represented by SEQ ID NO: 1.

In one embodiment, the recombinant vector may further comprise one or more selected from the group consisting of a transcriptional regulatory factor, a translational regulatory factor, and a marker for confirming gene expression.

In one embodiment, the transcriptional regulatory factor may be one or more selected from all transcription factors commonly used for transcriptional regulation in a cell, for example, a plant cell and may be, for example, one or more selected from the group consisting of a cauliflower mosaic virus 35S RNA promoter, a cauliflower mosaic virus 19S RNA promoter, a figwort mosaic virus-derived full-length transcription promoter, and a tobacco mosaic virus coat protein promoter, but the present invention is not limited thereto.

The translational regulatory factor may be one or more selected from all translational regulatory factors commonly used for translational regulation in a cell, for example, a plant cell and may be, for example, an M17 factor, but the present invention is not limited thereto. The M17 factor may have a nucleic acid sequence represented by SEQ ID NO: 3.

In another embodiment, the recombinant vector may further comprise a signal sequence for targeting (migration and/or retention) to a specific intracellular organelle. In one embodiment, the recombinant vector may be engineered to target the endoplasmic reticulum (ER), and to this end, may further comprise an endoplasmic reticulum (e.g., a cell membrane surface) transfer signal (e.g., a BiP (chaperone binding protein)-encoding gene or the like) and/or an endoplasmic reticulum retention signal (e.g., HDEL (His-Asp-Glu-Leu) (SEQ ID NO: 54) peptide-encoding gene). The signal sequence for targeting an intracellular organelle (e.g., an endoplasmic reticulum) may be linked to the N-terminal (5'-terminal of a gene encoding a fusion protein) or C-terminal (3'-terminal of the gene encoding a fusion protein), for example, N-terminal (5'-terminal of a gene encoding a fusion protein) of the fusion protein. As such, the recombinant vector may be targeted to the endoplasmic reticulum (e.g., inside the endoplasmic reticulum) of the intracellular organelle, thereby further increasing a protein expression level (see FIG. 3). In one embodiment, N-glycosylation of the fusion protein may occur in the endoplasmic reticulum.

The BiP (chaperone binding protein) may have a nucleic acid sequence represented by SEQ ID NO: 4.

In one embodiment, the present invention provides a recombinant vector for transforming a plant to increase an expression level of a target protein, the recombinant vector comprising a gene encoding the target protein, a gene encoding a human CD45-derived M domain, a transcriptional regulatory factor, an M17 factor operably linked to the transcriptional regulatory factor, and a gene encoding BiP (chaperone binding protein) and/or a HDEL (His-Asp-Glu-Leu) peptide.

In one embodiment, the recombinant vector may further comprise a marker for confirming gene expression. In one embodiment of the present invention, a HA epitope sequence was used to confirm the presence or absence of expression by western blotting, but the present invention is not limited thereto.

The eukaryotic cell described herein may be one or more selected from the group consisting of a fungus, an animal cell, and a plant cell, and may be, for example, a plant cell. The eukaryotic organism may be one or more selected from the group consisting of all unicellular eukaryotic organisms and multicellular eukaryotic organisms (plants or animals) and may be, for example, a plant. The plant described herein may be one or more plant selected from all algae, monocotyledonous plants, and dicotyledonous plants, or a cell thereof and may be, for example, a dicotyledonous plant selected from the group consisting of *Arabidopsis*, soybeans, tobacco, eggplants, peppers, potatoes, tomatoes, Korean cabbage, radish, cabbage, lettuce, peaches, pears, strawberries, watermelons, melons, cucumbers, carrots, and celery; a monocotyledonous plant selected from rice, barley, wheat, rye, corn, sugarcane, oats, and onions; or a cell thereof, but the present invention is not limited thereto.

The introduction of the recombinant vector into a eukaryotic organism (e.g., a plant) or a eukaryotic cell (e.g., a plant cell) may be performed using a general transduction method, for example, using one or more methods selected from the group consisting of an *Agrobacterium* sp.-mediated method, particle gun bombardment, silicon carbide whiskers, sonication, electroporation, and polyethylene glycol (PEG)-mediated transformation, but the present invention is not limited thereto.

As described above, the term "N-glycosylation" as used herein refers to a series of processes for binding glycans, which are sugar molecule oligosaccharides, to the nitrogen atom of an amino acid of a protein, and is distinguished from 0-glycosylation, which binds sugar molecules to the oxygen atom of an amino acid residue of a protein. In the present specification, N-glycosylation may occur in an endoplasmic reticulum (e.g., inside an endoplasmic reticulum).

The term "N-glycosylation domain" as used herein refers to a polypeptide comprising an N-glycosylation site (amino acid residue), which may be non-naturally occurring, e.g., chemically or recombinantly synthesized, or naturally occurring.

In one embodiment, a recombinant vector comprising a gene encoding a fusion protein produced by fusing a human CD45-derived M domain to the C-terminal of a target protein was prepared to be used in experiments, but the present invention is not limited thereto, and the human CD45-derived M domain may also be fused to the N-terminal of a target protein.

The fusion protein comprising a target protein and an N-glycosylation domain may comprise a suitable linker (e.g., a 1-50 aa, 1-30 aa, 1-20 aa, 2-50 aa, 2-30 aa, or 2-20 aa peptide linker) between the target protein and the N-glycosylation domain. The peptide linker may be a sequence in which glycine-serine is repeated, but the present invention is not limited thereto.

The amino acid sequences and nucleic acid sequences described herein may be construed as extending to a sequence with at least 70% homology, at least 75% homology, at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology, to the provided sequences.

The "% sequence homology" may be confirmed by comparing two optimized sequences using a comparison region, and some of the polynucleotide sequences in the comparison region may comprise an addition or deletion (i.e., a gap) compared to reference sequences (additions or deletions excluded) for the optimal alignment of two sequences.

The term "recombinant vector or recombinant cell" as used herein refers to a cell that replicates a heterologous nucleic acid (polynucleotide) or expresses the nucleic acid, or a vector or cell that expresses a protein encoded by a peptide, a heterologous peptide, or a heterologous nucleic acid. The recombinant cell may express a gene or gene segment that is not found in a natural form of the cell in one of a sense form and/or an antisense form. In addition, the recombinant cell may express a gene found in a cell in its natural state, but the gene is a modified form and a gene reintroduced into a cell by an artificial means.

The "recombinant vector" may be one or more selected from the group consisting of all plasmids, phage, yeast plasmids, plant cell viruses, mammalian cell viruses, and other media known in the art into which a gene sequence or nucleotide sequence can be inserted or introduced. Generally, any plasmid and vector may be used without particular limitation as long as it is capable of replicating and being stabilized in a plant cell or a plant host. In one embodiment, the recombinant vector may be for use in transforming a plant or a plant cell. The gene sequence or nucleotide sequence according to the present invention may be operably linked to an expression regulatory factor, and the expression regulatory factor operably linked to the gene sequence may be comprised in a single expression vector comprising both a selectable marker and a replication origin.

Examples of known vectors comprise pBI121, pHellsgate8, pROKII, pBI76, pET21, pSK(+), pLSAGPT, pUC, and pGEM. In addition, examples of vectors expressed in plants, which comprises a CMV35s promoter, comprise the pCAMBIA series (pCAMBIA1200, 1201, 1281, 1291, 1300, 1301, 1302, 1303, 1304, 1380, 1381, 2200, 2201, 2300, 2301, 3200, 3201, and 3300), pMDC32, and pC-TAPa-pYL436, but the present invention is not limited thereto.

The term "operably linked" as used herein may refer to a gene and an expression regulatory factor that are linked in such a way to enable gene expression when an appropriate molecule is bound to the expression regulatory factor.

The term "expression regulatory factor" as used herein refers to a DNA sequence that regulates the expression of a polynucleotide sequence operably linked in a particular host cell. Such regulatory factors comprise a transcriptional regulatory factor comprising a promoter for performing transcription and any operator sequence, a translational regulatory factor comprising a sequence encoding an appropriate mRNA ribosome-binding site and a sequence that regulates protein synthesis, and a sequence that regulates the termination of transcription and translation.

In the present invention, the transcriptional regulatory factor may be selected from the group consisting of a cauliflower mosaic virus 35S RNA promoter, a cauliflower mosaic virus 19S RNA promoter, a figwort mosaic virus-derived full-length transcription promoter, and a tobacco mosaic virus coat protein promoter, but the present invention is not limited thereto.

In the present invention, the translational regulatory factor may be an M17 sequence, which serves to increase the amount of a target protein synthesized in a plant. In the present invention, preferably, the M17 sequence may be represented by SEQ ID NO: 3.

The recombinant vector of the present invention may further comprise a nucleic acid encoding BiP (chaperone binding protein) or a HDEL (His-Asp-Glu-Leu) peptide, which may be operably linked to the transcriptional regulatory factor.

The BiP, which is a luminal binding protein, was identified as an immunoglobulin heavy chain binding protein and a glucose regulated protein, and is a member of the HSP70 chaperone family located in the endoplasmic reticulum and temporarily binds to a protein newly synthesized in the endoplasmic reticulum. In addition, BiP serves to enable target proteins to be targeted to the endoplasmic reticulum since it has, at the N-terminal thereof, a signal sequence that determines targeting to the endoplasmic reticulum. For example, a nucleic acid encoding the BiP may have a nucleic acid sequence represented by SEQ ID NO: 4.

In addition, the recombinant vector for transforming a plant may comprise a nucleotide sequence encoding an ER retention signal peptide such as HDEL. In the case of a HDEL signal peptide, a target protein is retained in the ER such that folding and assembly by a molecular chaperone are increased, resulting in further minimization of protein degradation. As an example, it is known that, in a case in which a target protein is retained more in the ER when sent to the secretory pathway, a yield of the target protein is increased about 10-fold to about 100-fold.

An embodiment also provides a recombinant vector for transforming a plant to increase an expression level of a target protein, the recombinant vector comprising a target protein, a gene encoding a human CD45-derived M domain or a portion thereof, a transcriptional regulatory factor, M17 operably linked to the transcriptional regulatory factor, and a nucleic acid encoding BiP (chaperone binding protein) and a HDEL (His-Asp-Glu-Leu) (SEQ ID NO: 54) peptide.

The recombinant vector described herein may further comprise a marker for confirming gene expression. In one embodiment, a HA epitope sequence was used to confirm expression by western blotting, but the present invention is not limited thereto.

The term "target protein" as used herein refers to a protein for producing or a fragment thereof, and the target protein is not limited to a specific protein. Specifically, the target protein may be any one or more selected from the group consisting of an antigen, an antibody, an antibody fragment, a structural protein, a regulatory protein, a transcription factor, a toxin protein, a hormone, a hormone analog, a cytokine, an enzyme, an enzyme inhibitor, a transport protein, a receptor (e.g., tyrosine kinase receptor and the like), a receptor fragment, a biological defense inducer, a storage protein, a movement protein, an exploitive protein, a reporter protein, and the like.

In one embodiment, leptin, GLP-1, Exendin-4, aprotinin, a green fluorescent protein (GFP), and the like have been described as examples of the target protein, but these are provided for illustrative purposes only to achieve a protein production-enhancing effect provided in the present specification, but the target protein is not limited to the above-listed proteins.

The present invention also provides a plant transformed with the recombinant vector. The transformed plant comprises an M domain sequence and is devised to be operably linked to transcriptional and translational regulatory factors and controlled thereby. The transformed plant described herein may be a whole plant, a plant cell (e.g., a cell such as a leaf, a stem, a root, and the like), or plant tissue (e.g., a leaf, a stem, a root, and the like). The plant tissue may comprise a plant seed. The plant may be an herbaceous or textured plant, and may be a dicotyledonous plant or a monocotyledonous plant. In particular, the dicotyledonous plant may be selected from the group consisting of *Arabidopsis*, soybeans, tobacco, eggplants, peppers, potatoes, tomatoes, Korean cabbage, radish, cabbage, lettuce, peaches, pears, strawberries, watermelons, melons, cucumbers, carrots, and celery, and the monocotyledonous plant may be selected from the group consisting of rice, barley, wheat, rye, corn, sugarcane, oats, and onions, but the present invention is not limited thereto.

A method of introducing the recombinant vector of the present invention into a plant may be selected from an *Agrobacterium* sp.-mediated method, particle gun bombardment, silicon carbide whiskers, sonication, electroporation, and polyethylene glycol (PEG)-mediated transformation, but the present invention is not limited thereto.

The transformed plant may be obtained through a sexual propagation method or an asexual propagation method, which is a conventional method in the art. More specifically, the plant of the present invention may be obtained through sexual propagation, which is a process of producing seeds through pollination and propagating from the seeds. In addition, the plant may be transformed with the recombinant vector according to the present invention and then obtained through asexual propagation, which is a process of inducing callus, rooting, and acclimatizing soil, according to a conventional method. That is, an explant of the plant transformed with the recombinant vector according to the present invention is placed in a suitable medium known in the art, and then cultured under appropriate conditions to induce callus formation, and when shoots are formed, they are transferred to a hormone-free medium and cultured. After about 2 weeks, the shoots are transferred to a rooting medium to induce roots. Thereafter, the roots may be transplanted into the soil and acclimatized, thereby obtaining the plant according to the present invention. The transformed plant of the present invention may comprise tissues, cells, or seeds obtainable therefrom.

The present invention also provides a method of producing a target protein, comprising: constructing a recombinant vector for transforming the plant; introducing the recombinant vector into a plant to produce a transgenic plant; culturing the transgenic plant; and isolating and purifying a target protein from the transgenic plant or a culture solution.

The introduction of the recombinant vector into a plant cell or a plant may be performed using one or more methods selected from the group consisting of an *Agrobacterium* sp.-mediated method, particle gun bombardment, silicon carbide whiskers, sonication, electroporation, and polyethylene glycol (PEG)-mediated transformation. In one embodiment of the present invention, PEG-mediated transformation was used.

Advantageous Effects

A recombinant vector for transforming a plant, according to the present invention, has overcome the difficulty of obtaining a highly expressed transformant, which was the biggest problem in protein production using existing plant transformation, by increasing an expression level of a target protein in a plant cell, and thus is expected to be great help in the production of useful proteins using a plant.

BRIEF DESCRIPTION OF DRAWINGS

FIG. 1 is a diagram illustrating a linkage comprising a p35S-M17: Bip: Leptin: M: HA: HDEL moiety in a recombinant vector for transforming a plant which was constructed according to an embodiment.

MODE OF THE INVENTION

Figure 2A:
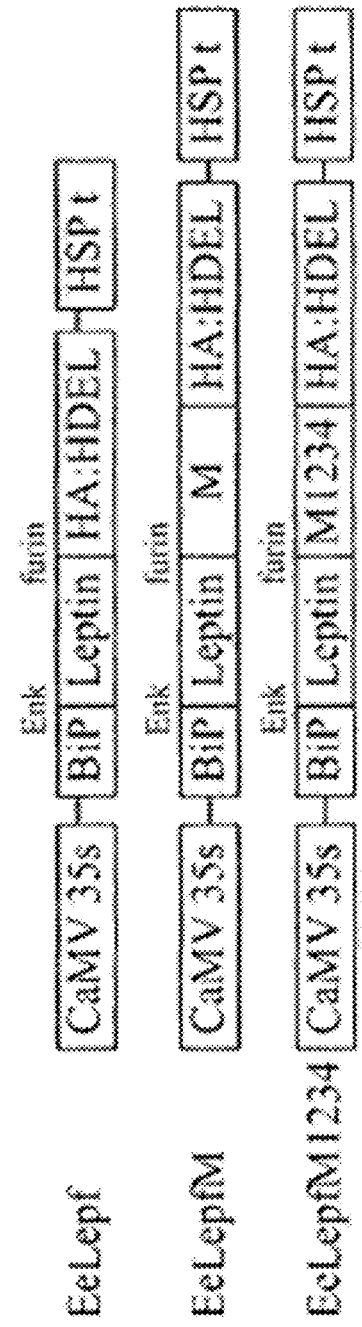
FIG. 2A is a diagram illustrating a linkage comprising a p35S-M17: Bip: Leptin: HA: HDEL moiety, a p35S-M17: Bip: Leptin: M: HA: HDEL moiety, and a p35S-M17: Bip: Leptin: M1234: HA: HDEL moiety in a recombinant vector for transforming a plant which was constructed according to an embodiment (M1234: M domain variant in which N-glycosylation sites N1, N2, N3, and N4 of an M domain were modified (Asn→Gln)).

Hereinafter, the present invention will be described in further detail with reference to the following examples.

It will be obvious to those of ordinary skill in the art that these examples are provided for illustrative purposes only and are not intended to limit the scope of the present invention.

Reference Example 1: Preparation of Plant Materials

Arabidopsis (*Arabidopsis thaliana* ecotype, Col-0) plants were grown on B5 plates in a growth chamber at 20° C. to 22° C. under a 16 h/8 h light/dark cycle. Leaf tissues from 2-week-old plants were used for protoplast isolation.

Reference Example 2: Plasmid Construction

The mature peptide region of mouse leptin cDNA (NM_008493.3) was used. A DNA fragment (SEQ ID NO: 1) encoding an M domain was synthesized by repetitive PCR, and mutants of the N-glycosylation (Asn-Gln substitution) were generated by PCR-based site-directed mutagenesis. A DNA fragment (SEQ ID NO: 11) encoding aprotinin was produced by chemical synthesis (Bioneer, Daejeon, Korea). Enterokinase and furin cleavage sites were included in the primer used for leptin amplification (5'-GGATCCAA-GATGATGATGATAAGGTGCC-TATCCAGAAAGTCCAGGAT-3' (SEQ ID NO: 18)). AHA epitope and an ER retention signal HDEL were introduced using the primers used for amplification of the M domain. PCR conditions were as follows: 94° C. for 5 minutes, (94° C. for 30 seconds, 52° C. for 1 minute, and 72° C. for 30 seconds) repeated 30 times, 72° C. for 7 minutes. The primer sequences used are summarized in Table 1 below:

TABLE 1

| Primer Name | Sequence (5' to 3') | SEQ ID NO. |
|---|---|---|
| BamHI-Ek-leptin-F | GGATCCAAGATGATGATGATAAGGTGCCTATCCAGAAAGTCCAGGAT | 18 |
| leptin-furin-SpeI-R | ACTAGTTCGCCTGACACGGCATTCAGGGCTAACATCCAACTG | 19 |
| hspt-R | GAATTCCTTATCTTTAATCATATT | 20 |
| M-3-HA-HDEL-F | TCATAATTCATGTACTGCTCCTGATTACCCATACGATGTTCCAGATTACGCTTCCCACGATGAGCTCTAGCTCGAGATATGAAGATGAAGATGAAATATT | 21 |
| M-2-F | AATGTGGAAACAATACTTGCACAAACAATGAGGTGCATAACCTTACAGAATGTAAAAATGCGTCTGTTTCCATATCTCATAATTCATGTACTGCTCCTGA | 22 |
| SpeI-M-1-F | ACTAGTGCAAACATCACTGTGGATTACTTATATAACAAGGAAACTAAATTATTTACAGCAAAGCTAAATGTTAATGAGAATGTGGAATGTGGAAACAATACTTGCACAA | 23 |
| SpeI-HA-F | ACTAGTTACCCATACGATGTTCCAGATTAC | 24 |
| XbaI-Cab-F | TCTAGAATGGCGTCGAACTCGCTTATGAGC | 25 |
| Cab-BamHI-R | GGATCCTCTCTGACTCTTTGTA | 26 |
| XbaI-F1-F | TCTAGAATGGCAATGGCTGTTTTCCGTCGC | 27 |

TABLE 1-continued

| Primer Name | Sequence (5' to 3') | SEQ ID NO. |
|---|---|---|
| F1-BamHI-R | GGATCCTCTGAACTGCTCTAAGCTTGGAAG | 28 |
| SpeI-M-F | ACTAGTGCAAACATCACTGTGGAT | 29 |
| SpeI-M-N2Q-F | ACTAGTGCACAAATCACTGTGGAT | 30 |
| M-N30Q-F | GTGGAATGTGGACAAAATACTTGCACA | 31 |
| M-N30Q-R | TGTGCAAGTATTTTGTCCACATTCCAC | 32 |
| M-N40Q-F | AATGAGGTGCATCAACTTACAGAATGT | 33 |
| M-N40Q-R | ACATTCTGTAAGTTGATGCACCTCATT | 34 |
| M-N46Q-F | ACAGAATGTAAACAAGCGTCTGTTTCC | 35 |
| M-N46Q-R | GGAAACAGACGCTTGTTTACATTCTGT | 36 |
| M-N40, 46Q-F | AACAATGAGGTGCATCAACTTACAGAATGTAAACAAGCGTCTGTTTCCATA | 37 |
| M-N40, 46Q-R | TATGGAAACAGACGCTTGTTTACATTCTGTAAGTTGATGCACCTCATTGTT | 38 |
| BamHI-M-F | GGATCCCGATGGCAAACATCACTGTGGATTACTTA | 39 |
| M-GS2-SpeI-R | ACTAGTTGATCCACCACCAGACCCACCTCCACCATCAGGAGCAGTACATGAATTAT | 40 |
| BamHI-Ek-Apr | GGATCCCGGATGACGACGATAAGCGACCGGAC | 41 |
| BamHI-ek-Apr-F | GGATCCAAGATGATGATGATAAGCGACCGGAC | 42 |
| Apr-fu-SpeI-R | ACTAGTTCGCCTGACACGGGCACCGCCGCAGGTTCTCATACA | 43 |
| GFP-HDEL-stop-XhoI-R | CTCGAGCTAGAGCTCATCGTGCTTGTACAGCTCGTCCATGCCGAG | 44 |
| GFP-fu-SpeI-R | ACTAGTTCGCCTGACACGCTTGTACAGCTCGTCCATGCCGAG | 45 |
| SpeI-ek-GFP-F | ACTAGTGATGACGACGATAGGTGAGCAAG | 46 |
| AtACT2-5' | TATGAATTACCCGATGGGCAAG | 47 |
| AtACT2-3' | TGGAACAAGACTTCTGGGCAT | 48 |
| leptin-F-qRT1-F | TCGGTATCCGCCAAGCAGTGCCTATCCAGAAAGTCCA | 49 |
| leptin-R-qRT1-R | GGTGAAGCCCAGGAATGAAGGCATTCAGGGCTAACATCCA | 50 |

The mature region of leptin and the M domain or Asn-to-Gln-substituted mutant M domain were sequentially ligated into the vector BiP: HA: CBD: HDEL.

To accumulate fusion proteins in chloroplasts and mitochondria, a Cab transit peptide or F1-ATPase gamma subunit presequence was amplified by PCR and substituted with BiP in EeLepf and EeLepfM vectors (see Lee, D., et al. W. et al., *Arabidopsis* nuclear-encoded plastid transit peptides contain multiple sequence subgroups with distinctive chloroplast-targeting sequence motifs. Plant Cell 20, 1603-1622 (2008); Lee, S. et al., Mitochondrial targeting of the *Arabidopsis* F1-ATPase gamma-subunit via multiple compensatory and synergistic presequence motifs. Plant Cell 24, 5037-5057 (2012)).

The constructs were all constructed from the same vector and therefore have the same 5'-UTRs. Nucleotide sequences of all PCR products were confirmed by nucleotide sequencing.

Reference Example 3: Expression, Compound Treatment, and Western Blotting Analysis The plasmid prepared in Reference Example 2 was introduced into a protoplast of plant cells prepared in Reference Example 1 by polyethylene glycol (PEG)-mediated transformation. After transformation, proteins were extracted at 24 hours or at a predetermined time to prepare protein extracts. Immediately after transformation, protoplasts were treated with tunicamycin (10 µg/mL; Sigma-Aldrich, St. Louis, Mo.) and then treated with cycloheximide (50 µg/mL; Sigma-Aldrich, St. Louis, Mo.) 12 hours after transformation. Western blotting analysis was performed on protein extracts using an anti-HA antibody (Roche Diagnostics, Indianapolis, Ind.), an anti-actin antibody (MP Biomedicals, Solon, Ohio), an anti-GFP antibody (Bio-Application, Pohang, Korea), or an anti-BiP antibody. Protein blots were developed with an ECL kit (Amersham Pharmacia Biotech, Piscataway, N.J.) and images were acquired using a LAS4000 image analyzer (Fujifilm, Tokyo, Japan).

Reference Example 4: Total RNA Isolation and Quantitative RT-PCR Analysis at Transcript Level Total RNA was extracted from PEG-mediated transformed plant protoplasts using an Ambion phenol-free total RNA isolation kit and treated with TURBO DNase (Ambion). cDNA was synthesized from the extracted total RNA using a high-capacity cDNA reverse transcription kit (Applied Biosystems). Transcript levels were detected using the Power SYBR Green PCR Master Mix (Applied Biosystems). ACTIN2 was used as an endogenous control. A PCR mixture (20 µl) contained 50 ng of a template, 0.5 mM forward and reverse primers, and 1×SYBR Mix.

PCR conditions were as follows: initial denaturation at 95° C. for 10 min, followed by 40 cycles of 95° C. for 15 s and 60° C. for 1 min.

To confirm specific amplification, a melting curve was generated by heating at 95° C. for 15 s and then at 60° C. for 1 min, and then increasing the temperature 0.3° C. every 15 sup to 95° C.

Example 1. Construction of Recombinant Vector for M Domain Fusion

To highly express a target protein in a plant, a recombinant vector for plant transformation which comprised a gene encoding a fusion protein in which the M domain of human CD45 was fused to the target protein was constructed. As the target protein, Leptin in which an enterokinase cleavage site and a furin cleavage site were fused to the N-terminal and the C-terminal, respectively (hereinafter referred to as "eLepf") was used. A CaMV 35S promoter was used in the vector pCAMBIA1300 as the recombinant vector, which is a commonly used vector, an M17 sequence (SEQ ID NO: 3) was added to increase the amount of protein synthesized, the target protein was transferred to an endoplasmic reticulum using a genomic DNA sequence (SEQ ID NO: 4) corresponding to a signal peptide of BiP (chaperone binding protein), and HDEL (His-Asp-Glu-Leu) (SEQ ID NO: 54) was added to the C-terminal to be retained in the endoplasmic reticulum so that the final target protein could be accumulated in the endoplasmic reticulum. In addition, the HA epitope was used to confirm the presence or absence of fusion protein expression by western blotting. A diagram of the recombinant vector constructed in the present example is shown in FIG. 1 (M: M domain).

A nucleic acid sequence (SEQ ID NO: 10) of the recombinant vector shown in FIG. 1 is summarized in Table 2 below.

TABLE 2

Nucleic acid sequence (SEQ ID NO: 10) of recombinant vector for expressing a Leptin-M domain fusion domain

| | Nucleic acid sequence (5'→3') |
|---|---|
| XbaI (Restriction enzyme site) | tctaga |
| M17 | ggcgtgtgtgtgtgttaaaga (SEQ ID NO: 3) |
| BiP | Atggctcgctcgtttggagctaacagtaccgttgtg ttggcgatcatcttcttcggtgagtgattttccgat cttcttctccgatttagatctcctctacattgttgc ttaatctcagaaccttttttcgttgttcctggatct gaatgtgtttgtttgcaatttcacgatcttaaaagg ttagatctcgattggtattgacgattggaatcttta cgatttcaggatgttatttgcgttgtcctctgcaa tagaagaggctacgaagttaa (SEQ ID NO: 4) |
| BamHI (Restriction enzyme site) open reading frame Enk (Enterokinase cleavage site) | ggatccaagatgatgatgataag (SEQ ID NO: 56) |
| Leptin | gtgcctatccagaaagtccaggatggcaccaaagcc ctcatcaagaccattgtcaccaggatcaatgacatt tcacacacgcagtcggtatccgccaagcagagggtc actggcttggacttcattcctgggcttcaccccatt ctgagtagtccaagatggaccagactctggcagtct atcaacaggtcctcaccagcctgccttcccaaaatg tgctgcagatagccaatgacctggagaatctccgag acctcctccatctgctggcttctccaagagctgct ccctgcctcagaccagtggcctgcagaagccagaga gcctggatggcgtcctggaagcctcactctactcca cagaggtggtggctttgagcaggctgcagggctctc tgcaggacattcttcaacagttggatgttagccctg aatgc (SEQ ID NO: 53) |
| furin cleavage site | cgtgtcaggcgaactagt (SEQ ID NO: 57) |
| SpeI (Restriction enzyme site) | |
| M | gcaaacatcactgtggattacttatatatagcaaac tctaaatgttaatgagaatgtggaatgtggaaacaa tacttgcacaaacaatgaggtgcataaccttacaga atgtaaaaatgcgtctgtaccatatctcataattca tgtactgctcctgat (SEQ ID NO: 1) |
| HA | tacccatacgatgttccagattacgct (SEQ ID NO: 58) |
| linker | tcc |
| HDEL | cacgatgagctc (SEQ ID NO: 9) |
| stop codon-XhoI | tagctcgag |

The N-glycosylation residues of an M domain of SEQ ID NO: 2 are as follows:

```
1                            30
ANITVDYLYNKETKLFTAKLNVNENVECGN
 N1                          N2

31                           60
NTCTNNEVHNLTECKNASVSISHNSCTAPD
         N3    N4
```

Example 2. Confirmation of Increased Protein Expression by N-Glycosylation of M Domain For comparison with an expression level of the fusion protein eLepfM produced by the recombinant vector comprising the M domain, constructed in Example 1, a recombinant vector was constructed as follows.

A vector EeLepf in which the M domain was removed from the recombinant vector (EeLepfM; see FIG. 1) of Example 1 and a vector EeLepfM1234 in which four N-glycosylation sites (Asn) of the M domain (see Example 1) were mutated (mutation; Asn was substituted with Gln) were constructed (see Reference Example 1). The three vectors (see FIG. 2A) were transformed into plant cells (see Reference Example 1) isolated from leaves of *Arabidopsis thaliana* via polyethylene glycol (PEG), and then treated with tunicamycin, which inhibits N-glycosylation, to confirm the effect of N-glycosylation. After 24 hours, protein expression levels were confirmed by western blotting. The results of the protein expression levels are shown in FIG. 2B (upper side: western blotting results; lower side: a graph showing results of quantifying the protein expression levels obtained as a result of western blotting, by using an LAS4000 image analyzer (Error bars, standard deviation (n=3); *, p<0.05 (Student's t-test)).

As illustrated in FIG. 2B, even when N-glycosylation did not occur, a protein expression level was increased when the M domain was fused (EeLepfM+tunicamycin), but when tunicamycin was not added to the recombinant vector comprising the M domain (EeLepfM−tunicamycin), N-glycosylation occurred and the expression level of the target protein was increased to a maximum degree.

To more clearly verify whether the increase in protein expression level due to the fusion of the M domain was induced by N-glycosylation, a recombinant vector was constructed such that the M domain-free target protein (eLepf) and the M domain-fused protein (eLepfM) were targeted to each of the endoplasmic reticulum, chloroplast, and mitochondria. To target the fusion proteins to each of the endoplasmic reticulum, chloroplast, and mitochondria, BiP (SEQ ID NO: 4), a Cab transit peptide (SEQ ID NO: 12), or F1-ATPase gamma subunit presequence (SEQ ID NO: 13) was fused to the N-terminal of the target protein, and an M domain-encoding nucleic acid sequence (SEQ ID NO: 1) was fused to the C-terminal of the target protein, thereby completing the construction of the recombinant vectors. Each recombinant vector was introduced into a plant cell using the above-described method, followed by culturing to express the corresponding fusion protein. Protein expression levels were confirmed by western blotting.

The results of the obtained protein expression levels are illustrated in FIG. 3 (upper side: a diagram of expression vectors; middle side: western blotting results; lower side: a graph showing results of quantifying the protein expression levels obtained as a result of western blotting by using an LAS4000 image analyzer (Error bars, standard deviation (n=3); *, p<0.05 (Student's t-test)).

As illustrated in FIG. 3, it was confirmed that, while the M domain-free eLepf showed no difference in protein amount according to an intracellular organelle, in the case of the M domain-fused eLepfM, the expression level of only EeLepfM targeted to the ER where N-glycosylation occurs was increased.

When the results of FIGS. 2B and 3 are taken together, it was confirmed that the increase in expression of the target protein due to the fusion of the M domain was caused by N-glycosylation.

Example 3. Expression Rate of M Domain-Fused Protein

As confirmed in Example 2, to understand the mechanism for the N-glycosylation-induced increase in protein expression, an expression rate of the M domain-fused protein was examined. Each of the M domain-fused recombinant vector EeLepfM and the vector EeLepfM1234 in which the N-glycosylation sites of the M domain were mutated was transformed into a plant cell, and after 12 hours, each vector was treated with cycloheximide or dimethyl sulfoxide (DMSO), which blocks protein synthesis, and then proteins were extracted at an interval of 12 hours to perform western blotting thereon.

The results thereof are illustrated in FIG. 4 (upper side: western blotting results; lower side: a graph showing results of quantifying the protein expression levels obtained as a result of western blotting by using an LAS4000 image analyzer (x-axis, time: Error bars, SD (n=3); *, p<0.05; ***, p<0.001).

As a result, as illustrated in FIG. 4, it was confirmed that there were almost no significant difference in expression levels of EeLepfM and EeLepfM1234 at the initial time (12 h), but the difference continued to increase over time, from which it was confirmed that the expression rate of EeLepfM was much faster than that of EeLepfM1234. However, it was confirmed that, while EeLepfM slightly disappeared in the plant cell when protein synthesis was blocked by treatment with cycloheximide, EeLepfM1234 was maintained as is up to 48 hours, from which it was confirmed that the fused protein EeLepfM1234 exhibited higher stability in the endoplasmic reticulum. These results indicate that a translation rate of a protein where N-glycosylation occurs is faster than that of a protein where no N-glycosylation occurs.

Example 4. Fusion of Various Proteins and M Domain

To confirm whether the expression increase effect due to the M domain is applicable to proteins other than the target protein (eLepf) used in the examples, the M domain-encoding gene (SEQ ID NO: 1) was fused to another target protein, e.g., a gene encoding Exendin4 (SEQ ID NO: 51) or a gene encoding GLP-1 (SEQ ID NO: 52), and a G domain, which is a translation enhancer domain, was fused thereto, thereby completing the construction of a recombinant vector (see FIG. 1). Each recombinant vector was transformed into a plant cell (see Reference Example 1), and then protein expression levels were confirmed by western blotting. The results thereof are illustrated in FIG. 5. As illustrated in FIG. 5, it was confirmed that the protein expression level was significantly increased when N-glycosylation occurred, due to no treatment with tunicamycin, as compared to when treated with tunicamycin that blocks N-glycosylation.

Example 5. Fusion of Various Proteins and M Domain in Various Orders

Figure 6A:
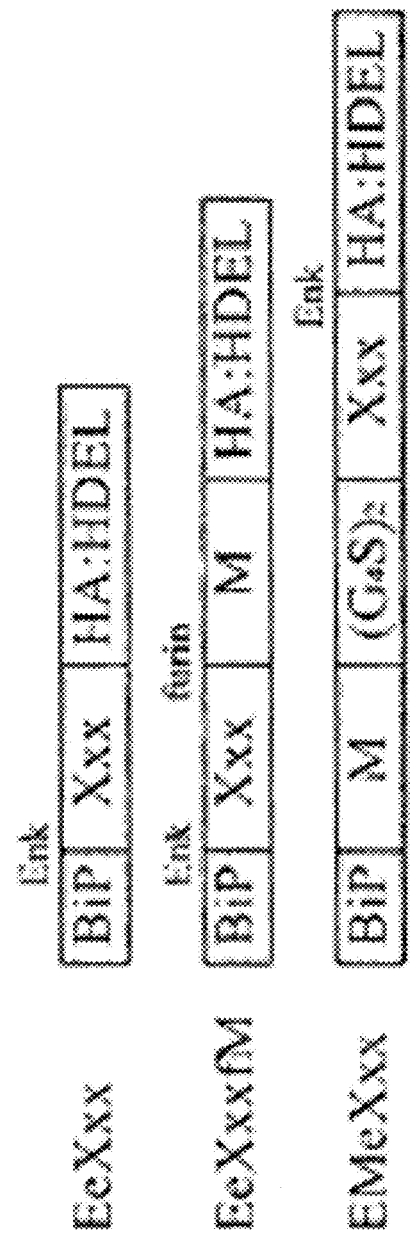
FIG. 6A is a diagram of a recombinant vector for expressing fusion proteins produced by fusing an M domain and various target proteins in various orders, according to an embodiment.

In addition, a recombinant vector comprising leptin (Lep), aprotinin (Apr; SEQ ID NO: 11), or GFP (Gfp; SEQ ID NO: 15) at the position Xxx of each of the recombinant vectors illustrated in FIG. 6A was prepared ("(G4S)2": linker (GGGGSGGGGS) (SEQ ID NO: 55)), and each recombinant vector was transformed into a plant cell, and then protein expression levels were confirmed by western blotting.

Figure 6B:
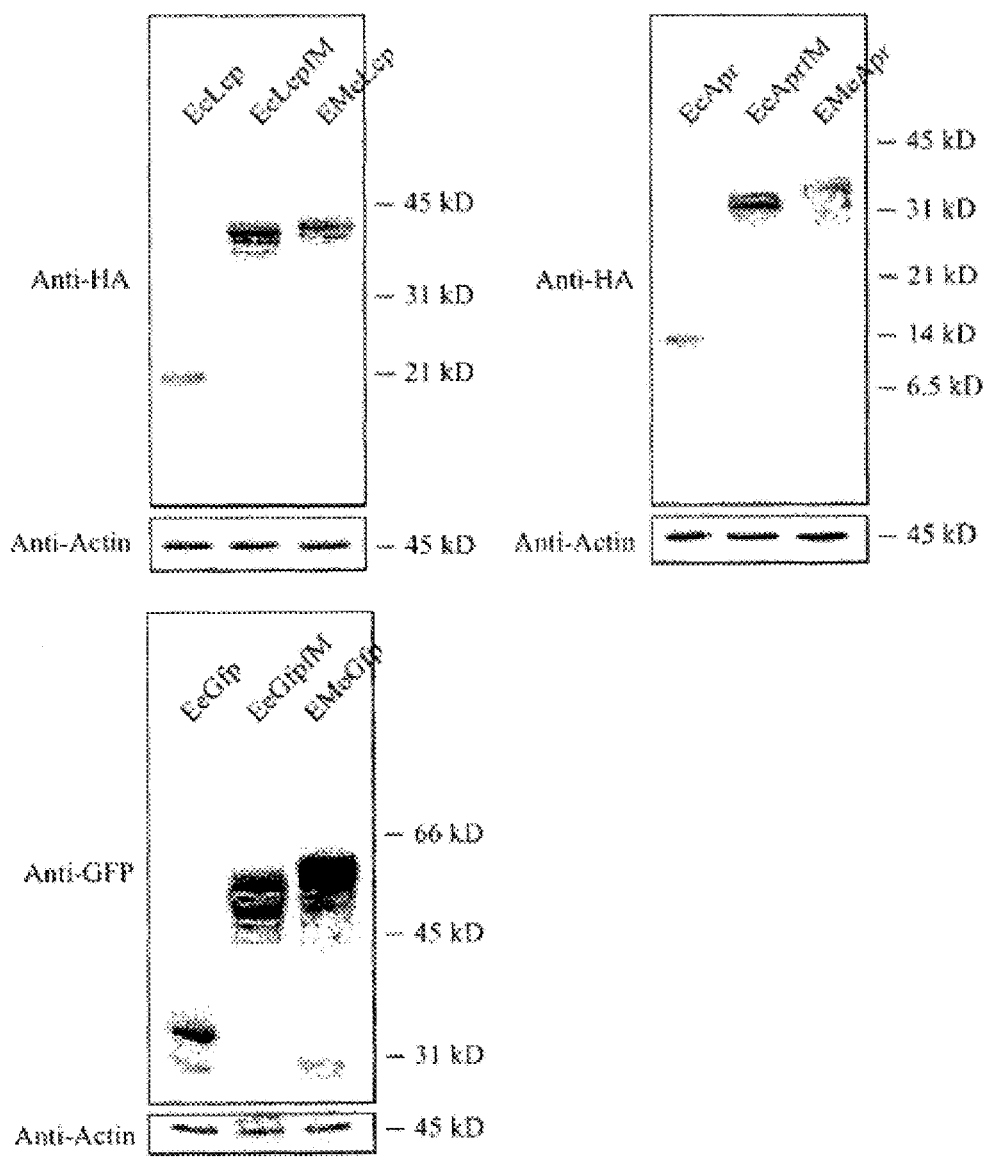
FIG. 6B illustrates western blotting results of confirming an expression level of a fusion protein produced by fusing an M domain and leptin (Lep), aprotinin (Apr), or GFP (Gfp) in various orders.

The results thereof are illustrated in FIG. 6B. As illustrated in FIG. 6B, it was confirmed that, when a gene encoding a fusion protein of a target protein and an M domain was expressed, an expression level of the target protein was significantly increased compared to when the M domain was not fused, regardless of the type of target protein, an order linked to the M domain, and the presence or absence of a linker.

Figure 7A:
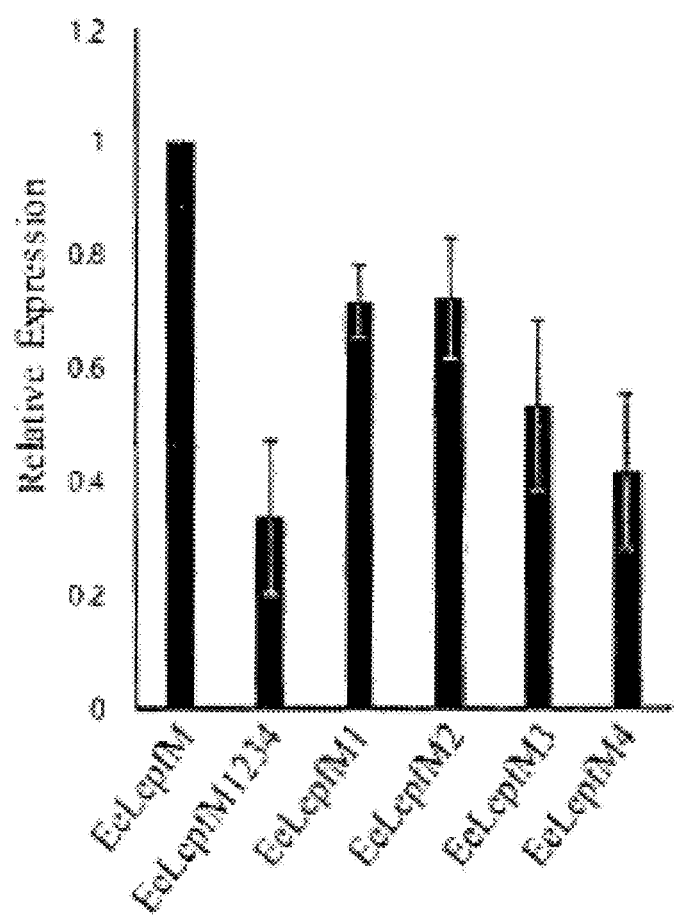
FIGS. 7A-7C is a set of graphs showing expression levels of fusion proteins in which Leptin was fused with each of mutant M domains where the N-glycosylation site of an M domain was mutated in various combinations.
Figure 7B:
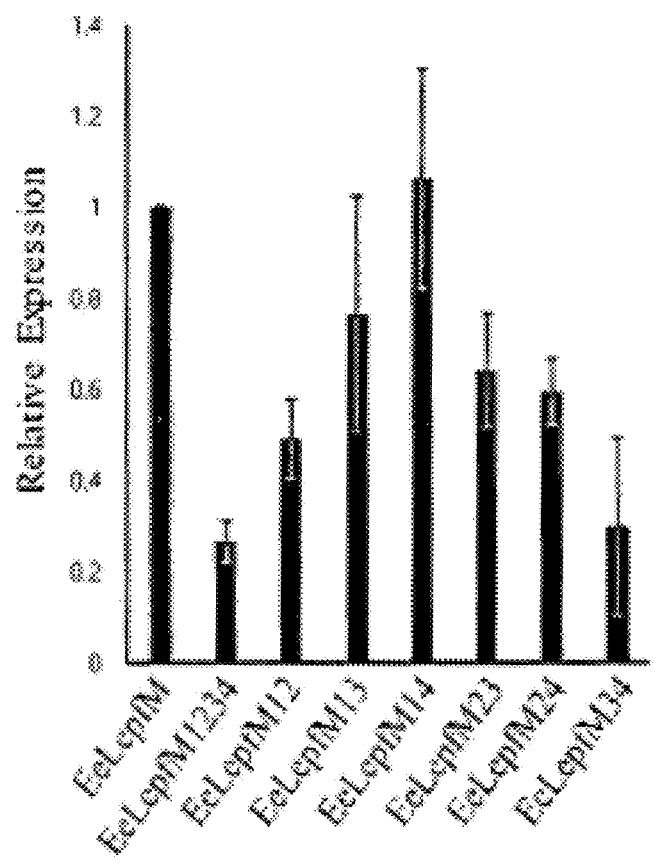
Figure 7C:
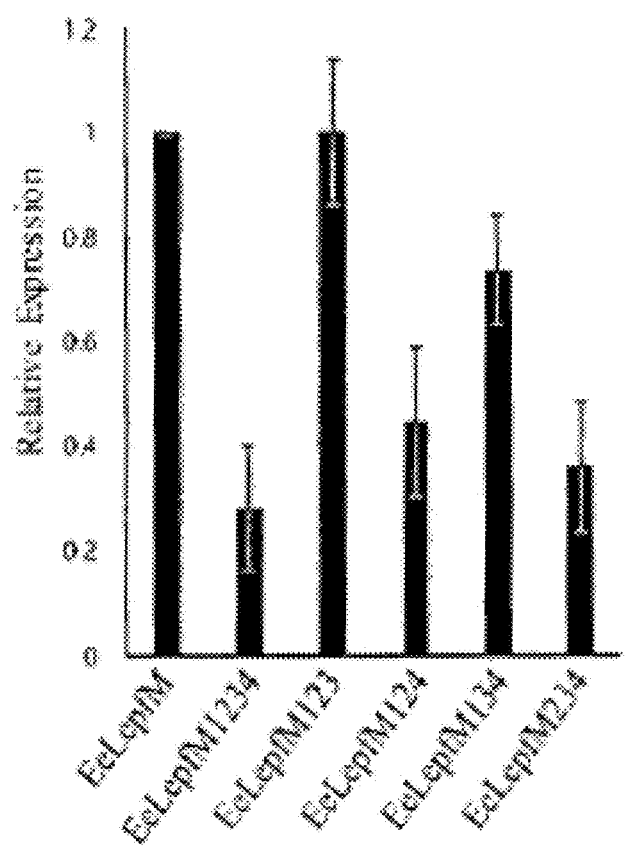

Example 6: Test of Target Protein Expression According to Combinations of N-Glycosylation Sites of M Domain The expression level of a target protein (Leptin) was measured using recombinant vectors comprising genes encoding mutants (one mutation, two mutations, three mutations, and all four mutations of the four N-glycosylation sites) into which Asn-Gln substitution mutation(s) was/were introduced to various combinations of the four N-glycosylation sites of the M domain (see the drawing of Example 1) (see FIGS. 7A-7C). Each recombinant vector was transformed into a protoplast of a plant cell, and then proteins were extracted, and the obtained protein extracts were analyzed by western blotting using an anti-HA antibody. The signal intensity of bands obtained as a result of western blotting was quantified using software provided with an LAS4000 image analyzer, and the results thereof are illustrated in FIGS. 7A-7C (on the x-axis, numbers following EeLepfM denote Asn-to-Gln mutated N-glycosylation sites). In FIGS. 7A-7C, the expression level of the target protein in a case in which each mutant was used was expressed as a relative value with respect to the expression level (1) of EeLepfM, which is an ER-targeted wild type protein (fusion of wild-type M domain and target protein). FIG. 7A illustrates relative expression levels of the target protein when single Asn-Gln mutants were used, FIG. 7B illustrates relative expression levels of the target protein when double Asn-Gln mutants were used, and FIG. 7C illustrates relative expression levels of the target protein when triple Asn-Gln mutants were used (Error bars, SD (n=4)).

Figure 2B:
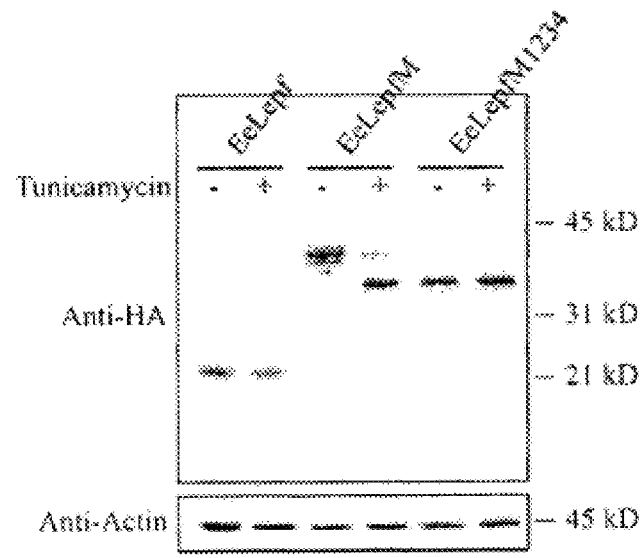
FIG. 2B illustrates electrophoresis results (upper side) of confirming protein expression levels by western blotting according to the presence or absence of N-glycosylation of an M domain and quantification results thereof (lower side).
Figure 2B:
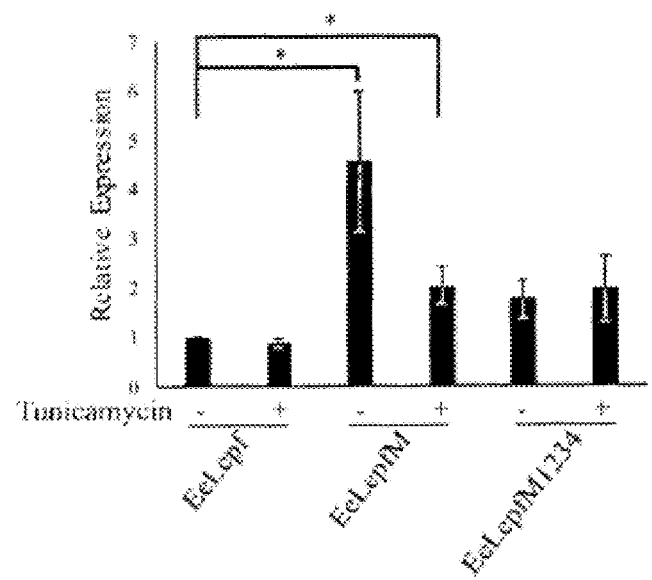
Figure 3:
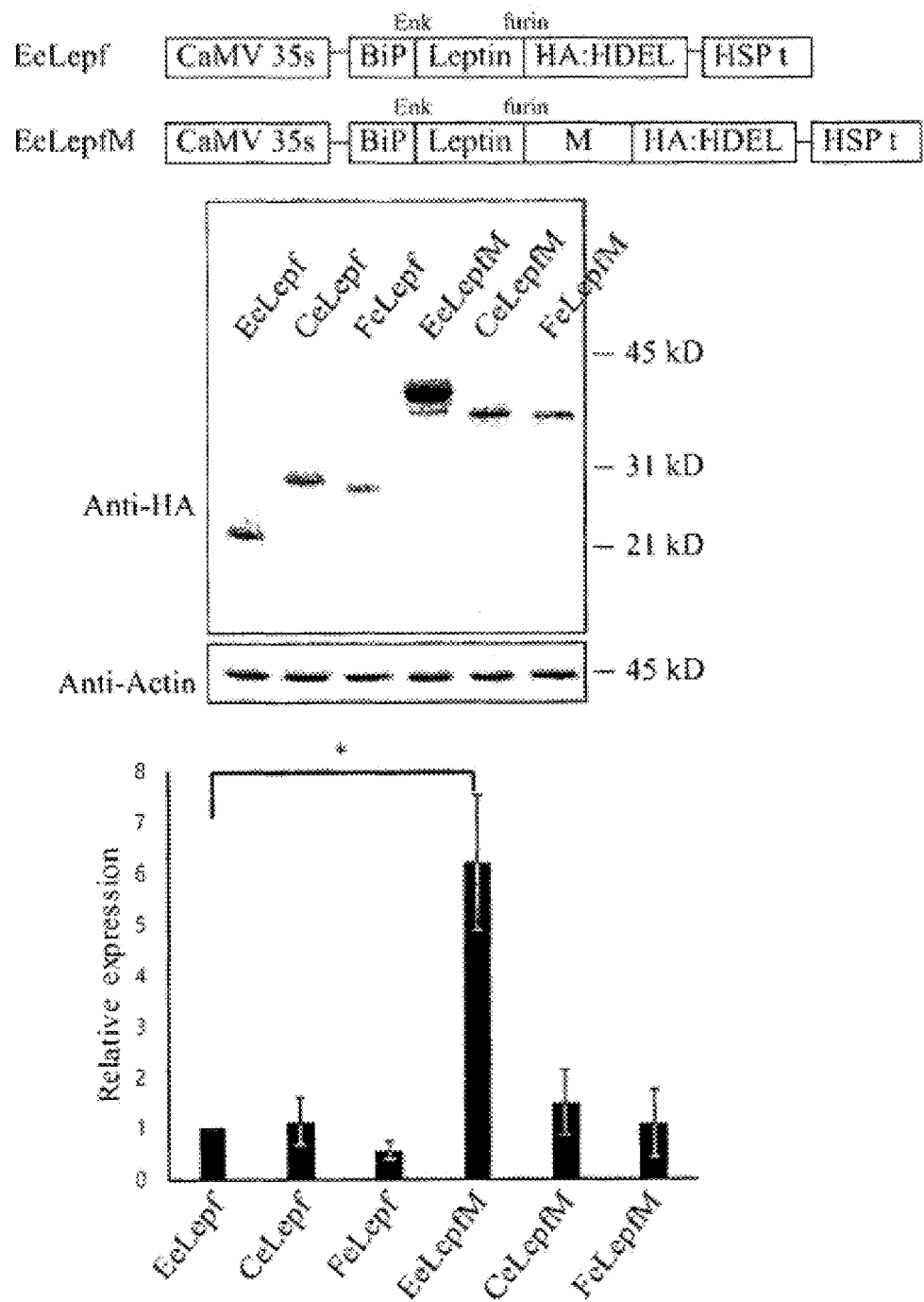
FIG. 3 is a diagram of a recombinant vector for testing a difference between protein expression levels according to a targeted plant cell organelle (upper side), and illustrates electrophoresis results (middle side) of confirming protein expression levels by western blotting and quantification results thereof (lower side).
Figure 4:
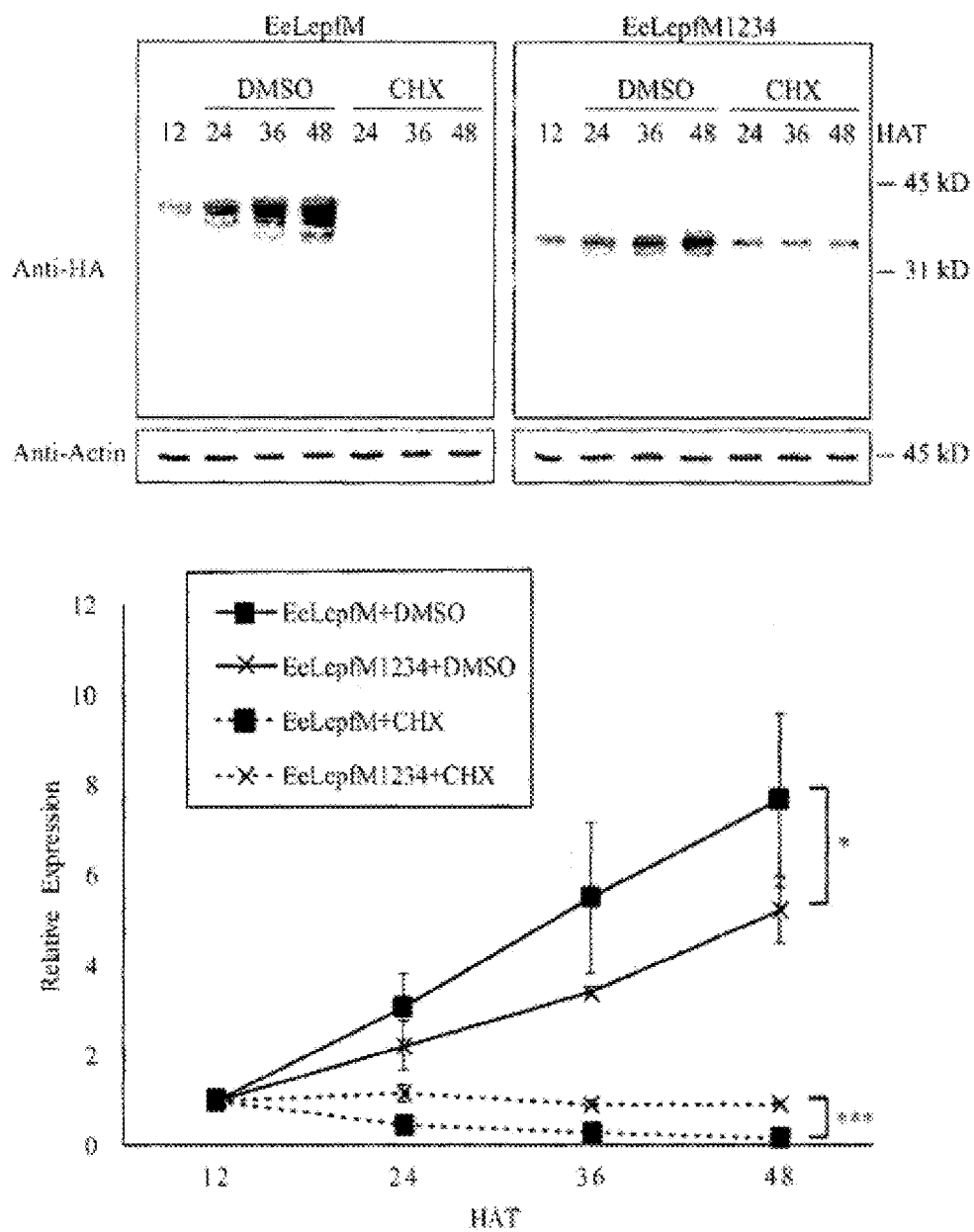
FIG. 4 illustrates electrophoresis results (upper side) of confirming expression patterns of fusion proteins fused with an M domain over time by western blotting and quantification results thereof (lower side).
Figure 5:
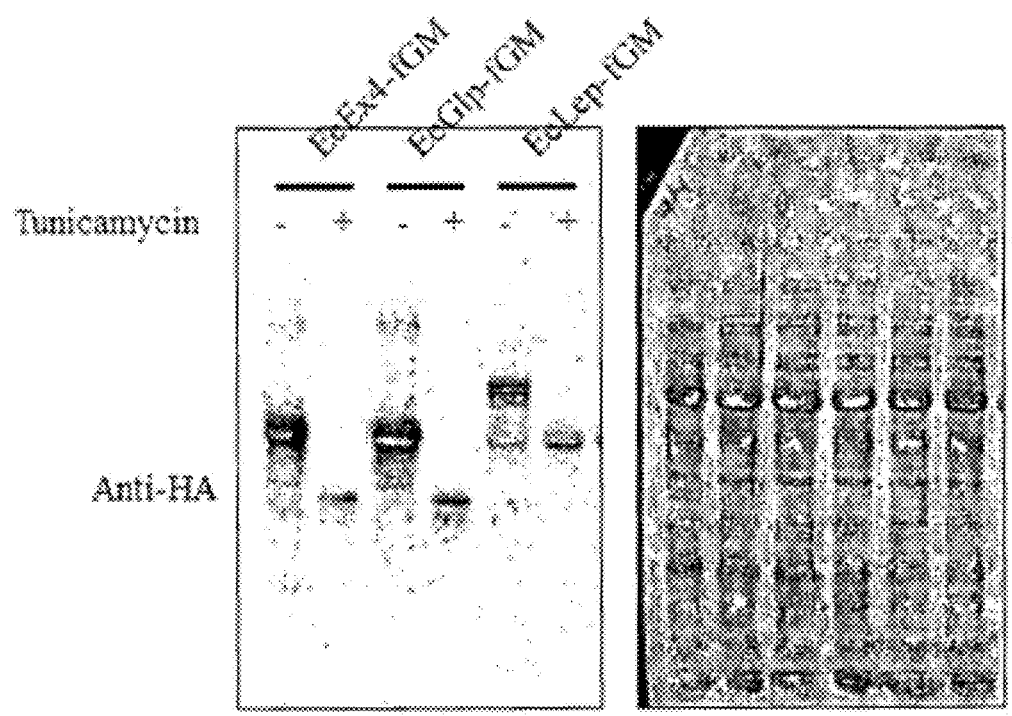
FIG. 5 illustrates western blotting results of confirming an expression level of a fusion protein produced by fusing an M domain with Exendin4 or GLP-1.

As illustrated in FIGS. 7A-7C, when mutation occurred at positions 1 to 3 of the N-glycosylation sites of the M domain, the expression level of the target protein was lower than that of wild type, but these cases exhibited a high expression level of the target protein compared to a case in which all four N-glycosylation sites were mutated. When considering that, even though a mutant in which all four N-glycosylation sites of the M domain were mutated was used, the expression level of the target protein was increased compared to a case in which the target protein was expressed alone (see FIG. 2B), even a case in which not only a wild-type M domain but also a mutant M domain in which mutations occurred at positions 1 to 4 of the four N-glycosylation sites may be considered to contribute to increasing the expression level of the fusion-expressed target protein.

Example 7: Test for Correlation Between Low Expression Level of Unglycosylated Protein and ER-Related Degradation It was tested whether the low expression level of an unglycosylated protein is related to ER-associated degradation. In conclusion, it was confirmed that the low expression level of the unglycosylated protein was not due to ER-associated degradation.

More specifically, each of the EeLepfM vector (expression of a fusion protein of Leptin and wild-type M domain) and EeLepfM1234 vector (expression of a fusion protein of Leptin and a mutant M domain in which all four glycosylation sites were mutated (substituted with Gln) was transformed into a plant protoplast, and then 20 μM MG132 (IUPAC name: Benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl]carbamate), which is an inhibitor of 26S proteasome-mediated degradation, was added to a protoplast culture medium at 18 h or 21 h, followed by further culturing of each protoplast for 6 hours or 3 hours.

[Schematic View of Test Design]

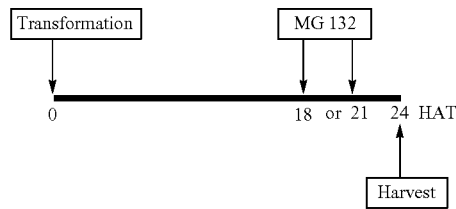

(HAT: Hours after Transformation)

For comparison (positive control), each protoplast was transformed with Rbcs[T4, 7A]: GFP, and then treated with MG132 at 18 h and further cultured for 6 hours. Rbcs[T4, 7A]: GFP, which is a GFP fusion construct, expresses a mutant form of the RbcS delivery peptide defective in the introduction of a protein into the chloroplast, and is ubiquitinated and degraded by the cytoplasmic 26S proteasome.

At 24 hours after transformation, proteins were extracted from each transformed protoplast, and then the protein extracts were analyzed by western blotting using an anti-HA antibody or an anti-GFP antibody.

Figure 8:
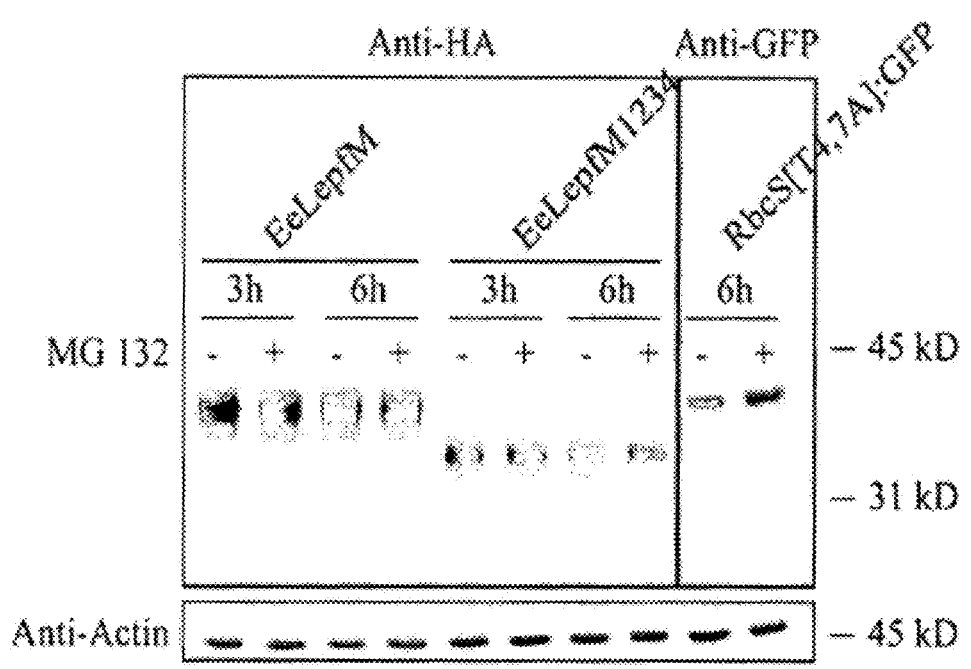
FIG. 8 illustrates western blotting results of confirming an expression level of a fusion protein fused with a wild type M domain or a mutant M domain according to the presence or absence of ER-associated degradation inhibition.

The obtained western blotting results are illustrated in FIG. 8. As illustrated in FIG. 8, the expression level of Rbcs[T4, 7A]: GFP was higher upon treatment with MG132, compared to non-treatment with MG132, and these results show that MG132 inhibits 26S proteasome-dependent protein degradation under test conditions of the present example. However, the expression levels of the EeLepfM and EeLepfM1234 proteins showed no difference regardless of MG132 treatment, which indicates that ER-associated degradation did not play a role in the expression of the N-glycosylated EeLepfM protein and the unglycosylated EeLepfM1234 protein.

Example 8: Test for Effect of N-Glycosylation of Target Protein Itself and N-Glycosylation of M Domain on Target Protein Expression It was examined whether the expression level of the target protein is increased even in the case of N-glycosylation of the target protein itself that was not fused with the M domain, that is, a case in which N-glycosylation of the target protein itself was possible due to its intrinsic inclusion of N-glycosylation sites.

To this end, with reference to the previous examples, an LIF (EeLiff)-expressing recombinant vector to which the M domain was fused or not fused was constructed using a leukemia inhibitory factor (LIF) (SEQ ID NO: 17; nucleic acid-encoding sequence: SEQ ID NO: 16; EeLiff; intrinsically having 6 N-glycosylation sites) instead of the Leptin protein, each recombinant vector was transformed into a plant protoplast, and after 24 hours, proteins were extracted and protein expression levels were measured by western blotting.

Figure 9:
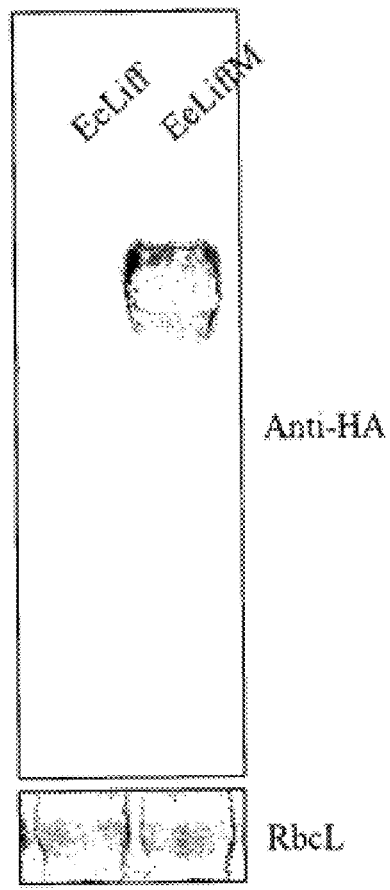
FIG. 9 illustrates western blotting results of confirming protein expression levels according to the presence or absence of fusion of a target protein intrinsically having an N-glycosylation site with an M domain.

The obtained protein expression levels are illustrated in FIG. 9. As illustrated in FIG. 9, it can be seen that the expression level of M domain-fused EeLiffM is significantly high compared to that of EeLiff to which the M domain was not fused (RbcL: loading control). These results show that, while N-glycosylation at N-glycosylation sites intrinsically comprised in the target protein does not affect the expression level of the target protein, N-glycosylation of the M domain, which is a fusion partner fused with the target protein, plays an important role in the expression level of the target protein.

Example 9: Expression Level of Fusion Protein Fused with Portion or Extension Portion of M Domain The expression level of a fusion protein in which the target protein (Leptin) was fused with a portion or extension portion of the M domain was tested. To this end, with reference to the method of Example 2, a fusion protein in which the target protein and a fragment (SEQ ID NO: 6) having a length of 20 amino acids at positions 41-60 of the M domain (SEQ ID NO: 2; total 60aa) (EeLepfM20; comprising 1 N-glycosylation site (N4: Asn at position 46), a fusion protein in which a fragment (SEQ ID NO: 7) having a length of 40 amino acids at positions 21-60 was fused (EeLepfM40; comprising 3 N-glycosylation sites of the M domain (N2: Asn at position 30; N3: Asn at position 40; and N4: Asn at position 46), and a fusion protein (E3LepfM80) in which a fragment (SEQ ID NO: 8) having a length of a total of 80 amino acids which extends by 10 amino acids towards each of the N-terminal and C-terminal of the M domain of SEQ ID NO: 2 in CD45 (SEQ ID NO: 5) were each introduced into a protoplast of a plant cell and expressed, and then proteins were extracted and expression levels thereof were measured by western blotting. For comparison, the expression level of EeLepf to which the M domain was not fused was also measured.

Figure 10:
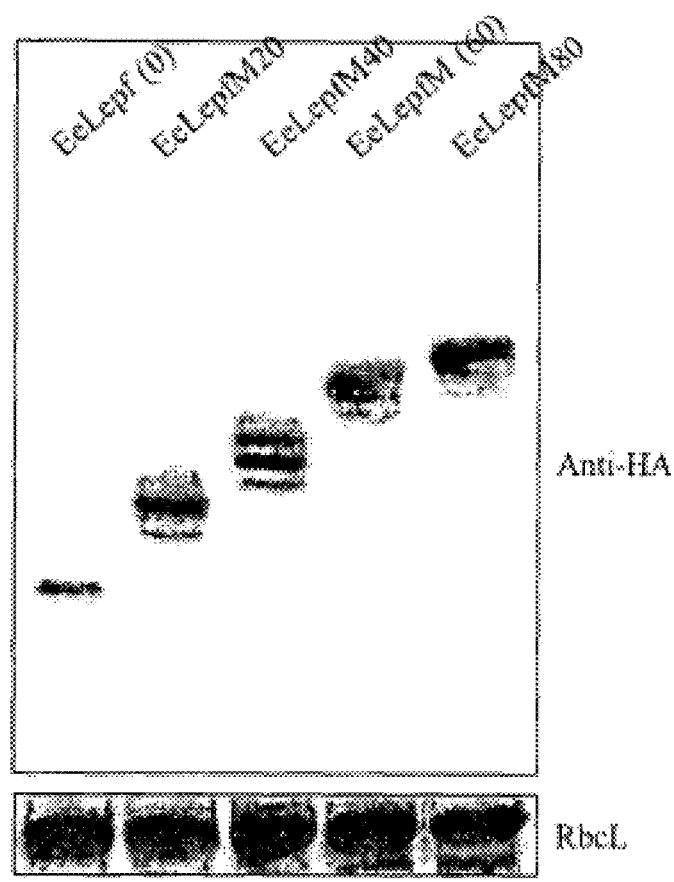
FIG. 10 illustrates western blotting results of confirming expression levels of fusion proteins produced by fusing a target protein with various M domain portions or extension portions.

The obtained protein expression levels are illustrated in FIG. 10. As illustrated in FIG. 10, all of EeLepfM20, EeLepfM40, EeLepfM60, and EeLepfM80 exhibited higher expression levels than that of EeLepf (EeLepf<<EeLepfM20<EeLepfM40≈EeLepfM≈EeLepfM80).

Example 10: Test for Transcript Level According to Fusion of M Domain or Various M Domain Mutants A plant cell (Reference Example 1) was transformed with each of recombinant vectors comprising a wild-type (not mutated) M domain or various M domain mutants in which each of the N-glycosylation sites was mutated and leptin, and total RNA was extracted after 1 day to perform quantitative RT-PCR. For a detailed method, refer to Reference Example 4.

Figure 11:
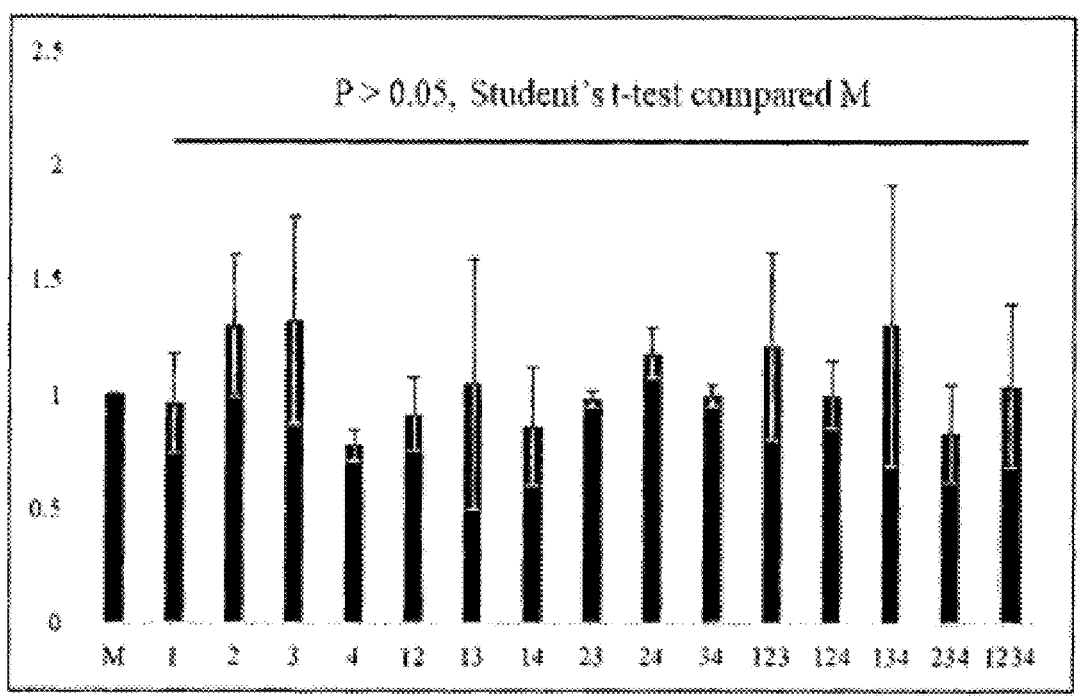
FIG. 11 is a graph showing quantitative RT-PCR results of confirming transcription levels according to fusion of an M domain or various M domain variants.

The obtained RNA levels are illustrated in FIG. 11. FIG. 11 illustrates mean values of mRNA levels in the case in which each M domain mutant was fused, relative to an mRNA level (=1) in the case in which a wild-type (not mutated) M domain (i.e., fully glycosylated) and leptin were fused with each other (Error bar, SD (n=3 for M to 14; n=2 for 23 to 1234). As a result of a Student's t-test, p values were equal to or greater than 0.05, which indicates that there was no difference in mRNA level between M domain-fused leptin and leptins to which mutated M domains were fused. These results indicate that the increase in expression due to fusion of the M domain is not due to an increase in mRNA level by increasing transcription, and suggests that such an expression increase is due to the promotion of translation from mRNA into a protein.

The invention claimed is:

1. A method of producing a target protein, the method comprising culturing a recombinant cell comprising a recombinant vector for expressing the target protein, the recombinant vector comprising a gene encoding a fusion protein comprising the target protein and an N-glycosylation domain fused to the C-terminal or N-terminal of the target protein, wherein the N-glycosylation domain is a polypeptide having a length of 10 to 60 consecutive amino acids in a human CD45 protein of SEQ ID NO: 5, the polypeptide consisting of a human CD45-derived M domain of SEQ ID NO: 2 or a portion of the M domain, wherein the portion of the M domain is a polypeptide fragment of 10 or more amino acids and one or more N-glycosylation sites selected from Asn at position 2, Asn at position 30, Asn at position 40, and Asn at position 46, of SEQ ID NO: 2.

2. The method of claim 1, wherein the polypeptide fragment selected from the group consisting of "LTECKNASVS ISHNSCTAPD (SEC) ID NO: 6)" and "NVNENVECGN NTCTNNEVHN LTECKNASVS ISHNSCTAPD (SEQ ID NO: 7)".

3. The method of 1, wherein the polypeptide fragment is "NVNENVECGN NTCTNNEVHN LTECKNASVS ISHNSCTAPD (SEQ ID NO: 7)".

4. The method of 1,
wherein the fusion protein further comprises a peptide linker between the target protein and the N-glycosylation domain.

5. The method of 1,
wherein the fusion protein is targeted to an endoplasmic reticulum.

6. The method of 1,
wherein the recombinant vector further comprises a BiP (chaperone binding protein)-encoding gene, a HDEL (His-Asp-Glu-Leu) (SEQ ID NO: 54) peptide-encoding gene, or a combination thereof.

7. The method of 1,
wherein the recombinant vector is for use in expression in a plant cell.

8. A method of producing a target protein, the method comprising growing a transgenic organism comprising a recombinant cell comprising a recombinant vector for expressing the target protein, the recombinant vector comprising a gene encoding a fusion protein comprising the target protein and an N-glycosylation domain fused to the C-terminal or N-terminal of the target protein, wherein the N-glycosylation domain is a polypeptide having a length of 10 to 60 consecutive amino acids in a human CD45 protein of SEQ ID NO: 5, the polypeptide consisting of a human CD45-derived M domain of SEQ ID NO: 2 or a portion of the M domain, wherein the portion of the M domain is a polypeptide fragment of 10 or more amino acids and one or more N-glycosylation sites selected from Asn at position 2, Asn at position 30, Asn at position 40, and Asn at position 46, of SEQ ID NO: 2.

9. The method of claim 8, the polypeptide fragment selected from the group consisting of "LTECKNASVS ISHNSCTAPD (SEQ ID NO: 6)" and "NVNENVECGN NTCTNNEVHN LTECKNASVS ISHNSCTAPD (SEQ ID NO: 7).

10. The method of 8, wherein the polypeptide fragment is "NVNENVECGN NTCTNNEVHN LTECKNASVS ISHNSCTAPD (SEQ ID NO: 7)".

11. The method of 8,
wherein the fusion protein further comprises a peptide linker between the target protein and the N-glycosylation domain.

12. The method of 8,
wherein the fusion protein is targeted to an endoplasmic reticulum.

13. The method of 8,
wherein the recombinant vector further comprises a BiP (chaperone binding protein)-encoding gene, a HDEL (His-Asp-Glu-Leu) (SEQ ID NO: 54) peptide-encoding gene, or a combination thereof.

14. The method of 8,
wherein the recombinant vector is for use in expression in a plant cell.

* * * * *

SEQUENCE LISTING

```
<160> NUMBER OF SEQ ID NOS: 53

<210> SEQ ID NO 1
<211> LENGTH: 180
<212> TYPE: DNA
<213> ORGANISM: Artificial Sequence
<220> FEATURE:
<223> OTHER INFORMATION: M domain coding nucleic acid sequence

<400> SEQUENCE: 1
gcaaacatca ctgtggatta cttatataac aaggaaacta aattatttac agcaaagcta      60
aatgttaatg agaatgtgga atgtggaaac aatacttgca caaacaatga ggtgcataac     120
cttacagaat gtaaaaatgc gtctgtttcc atatctcata attcatgtac tgctcctgat     180

<210> SEQ ID NO 2
<211> LENGTH: 60
<212> TYPE: PRT
<213> ORGANISM: Artificial Sequence
<220> FEATURE:
<223> OTHER INFORMATION: M domain
```

<400> SEQUENCE: 2

Ala Asn Ile Thr Val Asp Tyr Leu Tyr Asn Lys Glu Thr Lys Leu Phe
1               5                   10                  15

Thr Ala Lys Leu Asn Val Asn Glu Asn Val Glu Cys Gly Asn Asn Thr
            20                  25                  30

Cys Thr Asn Asn Glu Val His Asn Leu Thr Glu Cys Lys Asn Ala Ser
        35                  40                  45

Val Ser Ile Ser His Asn Ser Cys Thr Ala Pro Asp
    50                  55                  60

<210> SEQ ID NO 3
<211> LENGTH: 21
<212> TYPE: DNA
<213> ORGANISM: Artificial Sequence
<220> FEATURE:
<223> OTHER INFORMATION: M17

<400> SEQUENCE: 3
ggcgtgtgtg tgtgttaaag a                                         21

<210> SEQ ID NO 4
<211> LENGTH: 273
<212> TYPE: DNA
<213> ORGANISM: Artificial Sequence
<220> FEATURE:
<223> OTHER INFORMATION: BiP(chaperone binding protein) coding nucleic
      acid sequence

<400> SEQUENCE: 4
atggctcgct cgtttggagc taacagtacc gttgtgttgg cgatcatctt cttcggtgag      60 tgatttccg atcttcttct ccgatttaga tctcctctac attgttgctt aatctcagaa     120
ccttttttcg ttgttcctgg atctgaatgt gtttgtttgc aatttcacga tcttaaaagg    180
ttagatctcg attggtattg acgattggaa tctttacgat ttcaggatgt ttatttgcgt    240
tgtcctctgc aatagaagag gctacgaagt taa                                 273

<210> SEQ ID NO 5
<211> LENGTH: 1304
<212> TYPE: PRT
<213> ORGANISM: Artificial Sequence
<220> FEATURE:
<223> OTHER INFORMATION: human CD45

<400> SEQUENCE: 5

Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
            20                  25                  30

Leu Thr Thr Ala Lys Met Pro Ser Val Pro Leu Ser Ser Asp Pro Leu
        35                  40                  45

Pro Thr His Thr Thr Ala Phe Ser Pro Ala Ser Thr Phe Glu Arg Glu
    50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
            85                  90                  95

Thr Gly Val Ser Ser Val Gln Thr Pro His Leu Pro Thr His Ala Asp
        100                 105                 110

Ser Gln Thr Pro Ser Ala Gly Thr Asp Thr Gln Thr Phe Ser Gly Ser

-continued

```
            115                 120                 125
Ala Ala Asn Ala Lys Leu Asn Pro Thr Pro Gly Ser Asn Ala Ile Ser
        130                 135                 140
Asp Val Pro Gly Glu Arg Ser Thr Ala Ser Thr Phe Pro Thr Asp Pro
145                 150                 155                 160
Val Ser Pro Leu Thr Thr Thr Leu Ser Leu Ala His His Ser Ser Ala
                165                 170                 175
Ala Leu Pro Ala Arg Thr Ser Asn Thr Thr Ile Thr Ala Asn Thr Ser
            180                 185                 190
Asp Ala Tyr Leu Asn Ala Ser Glu Thr Thr Thr Leu Ser Pro Ser Gly
            195                 200                 205
Ser Ala Val Ile Ser Thr Thr Thr Ile Ala Thr Thr Pro Ser Lys Pro
        210                 215                 220
Thr Cys Asp Glu Lys Tyr Ala Asn Ile Thr Val Asp Tyr Leu Tyr Asn
225                 230                 235                 240
Lys Glu Thr Lys Leu Phe Thr Ala Lys Leu Asn Val Asn Glu Asn Val
                245                 250                 255
Glu Cys Gly Asn Asn Thr Cys Thr Asn Asn Glu Val His Asn Leu Thr
            260                 265                 270
Glu Cys Lys Asn Ala Ser Val Ser Ile Ser His Asn Ser Cys Thr Ala
            275                 280                 285
Pro Asp Lys Thr Leu Ile Leu Asp Val Pro Pro Gly Val Glu Lys Phe
        290                 295                 300
Gln Leu His Asp Cys Thr Gln Val Glu Lys Ala Asp Thr Thr Ile Cys
305                 310                 315                 320
Leu Lys Trp Lys Asn Ile Glu Thr Phe Thr Cys Asp Thr Gln Asn Ile
                325                 330                 335
Thr Tyr Arg Phe Gln Cys Gly Asn Met Ile Phe Asp Asn Lys Glu Ile
            340                 345                 350
Lys Leu Glu Asn Leu Glu Pro Glu His Glu Tyr Lys Cys Asp Ser Glu
            355                 360                 365
Ile Leu Tyr Asn Asn His Lys Phe Thr Asn Ala Ser Lys Ile Ile Lys
        370                 375                 380
Thr Asp Phe Gly Ser Pro Gly Glu Pro Gln Ile Ile Phe Cys Arg Ser
385                 390                 395                 400
Glu Ala Ala His Gln Gly Val Ile Thr Trp Asn Pro Pro Gln Arg Ser
                405                 410                 415
Phe His Asn Phe Thr Leu Cys Tyr Ile Lys Glu Thr Glu Lys Asp Cys
            420                 425                 430
Leu Asn Leu Asp Lys Asn Leu Ile Lys Tyr Asp Leu Gln Asn Leu Lys
            435                 440                 445
Pro Tyr Thr Lys Tyr Val Leu Ser Leu His Ala Tyr Ile Ile Ala Lys
        450                 455                 460
Val Gln Arg Asn Gly Ser Ala Ala Met Cys His Phe Thr Thr Lys Ser
465                 470                 475                 480
Ala Pro Pro Ser Gln Val Trp Asn Met Thr Val Ser Met Thr Ser Asp
                485                 490                 495
Asn Ser Met His Val Lys Cys Arg Pro Pro Arg Asp Arg Asn Gly Pro
            500                 505                 510
His Glu Arg Tyr His Leu Glu Val Glu Ala Gly Asn Thr Leu Val Arg
            515                 520                 525
Asn Glu Ser His Lys Asn Cys Asp Phe Arg Val Lys Asp Leu Gln Tyr
        530                 535                 540
```

```
Ser Thr Asp Tyr Thr Phe Lys Ala Tyr Phe His Asn Gly Asp Tyr Pro
545                 550                 555                 560

Gly Glu Pro Phe Ile Leu His His Ser Thr Ser Tyr Asn Ser Lys Ala
                565                 570                 575

Leu Ile Ala Phe Leu Ala Phe Leu Ile Ile Val Thr Ser Ile Ala Leu
                580                 585                 590

Leu Val Val Leu Tyr Lys Ile Tyr Asp Leu His Lys Lys Arg Ser Cys
                595                 600                 605

Asn Leu Asp Glu Gln Gln Glu Leu Val Glu Arg Asp Asp Glu Lys Gln
610                 615                 620

Leu Met Asn Val Glu Pro Ile His Ala Asp Ile Leu Leu Glu Thr Tyr
625                 630                 635                 640

Lys Arg Lys Ile Ala Asp Glu Gly Arg Leu Phe Leu Ala Glu Phe Gln
                645                 650                 655

Ser Ile Pro Arg Val Phe Ser Lys Phe Pro Ile Lys Glu Ala Arg Lys
                660                 665                 670

Pro Phe Asn Gln Asn Lys Asn Arg Tyr Val Asp Ile Leu Pro Tyr Asp
            675                 680                 685

Tyr Asn Arg Val Glu Leu Ser Glu Ile Asn Gly Asp Ala Gly Ser Asn
690                 695                 700

Tyr Ile Asn Ala Ser Tyr Ile Asp Gly Phe Lys Glu Pro Arg Lys Tyr
705                 710                 715                 720

Ile Ala Ala Gln Gly Pro Arg Asp Glu Thr Val Asp Asp Phe Trp Arg
                725                 730                 735

Met Ile Trp Glu Gln Lys Ala Thr Ile Val Met Val Thr Arg Cys
                740                 745                 750

Glu Glu Gly Asn Arg Asn Lys Cys Ala Glu Tyr Trp Pro Ser Met Glu
                755                 760                 765

Glu Gly Thr Arg Ala Phe Gly Asp Val Val Lys Ile Asn Gln His
            770                 775                 780

Lys Arg Cys Pro Asp Tyr Ile Ile Gln Lys Leu Asn Ile Val Asn Lys
785                 790                 795                 800

Lys Glu Lys Ala Thr Gly Arg Glu Val Thr His Ile Gln Phe Thr Ser
                805                 810                 815

Trp Pro Asp His Gly Val Pro Glu Asp Pro His Leu Leu Leu Lys Leu
                820                 825                 830

Arg Arg Arg Val Asn Ala Phe Ser Asn Phe Phe Ser Gly Pro Ile Val
            835                 840                 845

Val His Cys Ser Ala Gly Val Gly Arg Thr Gly Thr Tyr Ile Gly Ile
        850                 855                 860

Asp Ala Met Leu Glu Gly Leu Glu Ala Glu Asn Lys Val Asp Val Tyr
865                 870                 875                 880

Gly Tyr Val Val Lys Leu Arg Arg Gln Arg Cys Leu Met Val Gln Val
                885                 890                 895

Glu Ala Gln Tyr Ile Leu Ile His Gln Ala Leu Val Glu Tyr Asn Gln
            900                 905                 910

Phe Gly Glu Thr Glu Val Asn Leu Ser Glu Leu His Pro Tyr Leu His
            915                 920                 925

Asn Met Lys Lys Arg Asp Pro Pro Ser Glu Pro Ser Pro Leu Glu Ala
            930                 935                 940

Glu Phe Gln Arg Leu Pro Ser Tyr Arg Ser Trp Arg Thr Gln His Ile
945                 950                 955                 960
```

Gly Asn Gln Glu Glu Asn Lys Ser Lys Asn Arg Asn Ser Asn Val Ile
            965                 970                 975

Pro Tyr Asp Tyr Asn Arg Val Pro Leu Lys His Glu Leu Glu Met Ser
        980                 985                 990

Lys Glu Ser Glu His Asp Ser Asp Glu Ser Ser Asp Asp Asp Ser Asp
    995                 1000                1005

Ser Glu Glu Pro Ser Lys Tyr Ile Asn Ala Ser Phe Ile Met Ser Tyr
   1010                1015                1020

Trp Lys Pro Glu Val Met Ile Ala Ala Gln Gly Pro Leu Lys Glu Thr
1025                1030                1035                1040

Ile Gly Asp Phe Trp Gln Met Ile Phe Gln Arg Lys Val Lys Val Ile
                1045                1050                1055

Val Met Leu Thr Glu Leu Lys His Gly Asp Gln Glu Ile Cys Ala Gln
            1060                1065                1070

Tyr Trp Gly Glu Gly Lys Gln Thr Tyr Gly Asp Ile Glu Val Asp Leu
        1075                1080                1085

Lys Asp Thr Asp Lys Ser Ser Thr Tyr Thr Leu Arg Val Phe Glu Leu
    1090                1095                1100

Arg His Ser Lys Arg Lys Asp Ser Arg Thr Val Tyr Gln Tyr Gln Tyr
1105                1110                1115                1120

Thr Asn Trp Ser Val Glu Gln Leu Pro Ala Glu Pro Lys Glu Leu Ile
                1125                1130                1135

Ser Met Ile Gln Val Val Lys Gln Lys Leu Pro Gln Lys Asn Ser Ser
            1140                1145                1150

Glu Gly Asn Lys His His Lys Ser Thr Pro Leu Leu Ile His Cys Arg
        1155                1160                1165

Asp Gly Ser Gln Gln Thr Gly Ile Phe Cys Ala Leu Leu Asn Leu Leu
    1170                1175                1180

Glu Ser Ala Glu Thr Glu Glu Val Val Asp Ile Phe Gln Val Val Lys
1185                1190                1195                1200

Ala Leu Arg Lys Ala Arg Pro Gly Met Val Ser Thr Phe Glu Gln Tyr
                1205                1210                1215

Gln Phe Leu Tyr Asp Val Ile Ala Ser Thr Tyr Pro Ala Gln Asn Gly
            1220                1225                1230

Gln Val Lys Lys Asn His Gln Glu Asp Lys Ile Glu Phe Asp Asn
        1235                1240                1245

Glu Val Asp Lys Val Lys Gln Asp Ala Asn Cys Val Asn Pro Leu Gly
    1250                1255                1260

Ala Pro Glu Lys Leu Pro Glu Ala Lys Glu Gln Ala Glu Gly Ser Glu
1265                1270                1275                1280

Pro Thr Ser Gly Thr Glu Gly Pro Glu His Ser Val Asn Gly Pro Ala
                1285                1290                1295

Ser Pro Ala Leu Asn Gln Gly Ser
            1300

<210> SEQ ID NO 6
<211> LENGTH: 20
<212> TYPE: PRT
<213> ORGANISM: Artificial Sequence
<220> FEATURE:
<223> OTHER INFORMATION: Part of M domain

<400> SEQUENCE: 6

Leu Thr Glu Cys Lys Asn Ala Ser Val Ser Ile Ser His Asn Ser Cys
1               5                   10                  15

Thr Ala Pro Asp
        20

<210> SEQ ID NO 7
<211> LENGTH: 40
<212> TYPE: PRT
<213> ORGANISM: Artificial Sequence
<220> FEATURE:
<223> OTHER INFORMATION: Part of M domain

<400> SEQUENCE: 7

Asn Val Asn Glu Asn Val Glu Cys Gly Asn Asn Thr Cys Thr Asn Asn
1               5                  10                  15

Glu Val His Asn Leu Thr Glu Cys Lys Asn Ala Ser Val Ser Ile Ser
            20                  25                  30

His Asn Ser Cys Thr Ala Pro Asp
        35                  40

<210> SEQ ID NO 8
<211> LENGTH: 80
<212> TYPE: PRT
<213> ORGANISM: Artificial Sequence
<220> FEATURE:
<223> OTHER INFORMATION: Extended M domain

<400> SEQUENCE: 8

Pro Ser Lys Pro Thr Cys Asp Glu Lys Tyr Ala Asn Ile Thr Val Asp
1               5                  10                  15

Tyr Leu Tyr Asn Lys Glu Thr Lys Leu Phe Thr Ala Lys Leu Asn Val
            20                  25                  30

Asn Glu Asn Val Glu Cys Gly Asn Asn Thr Cys Thr Asn Asn Glu Val
        35                  40                  45

His Asn Leu Thr Glu Cys Lys Asn Ala Ser Val Ser Ile Ser His Asn
    50                  55                  60

Ser Cys Thr Ala Pro Asp Lys Thr Leu Ile Leu Asp Val Pro Pro Gly
65                  70                  75                  80

<210> SEQ ID NO 9
<211> LENGTH: 12
<212> TYPE: DNA
<213> ORGANISM: Artificial Sequence
<220> FEATURE:
<223> OTHER INFORMATION: HDEL coding nucleic acid sequence

<400> SEQUENCE: 9
cacgatgagc tc                                                         12

<210> SEQ ID NO 10
<211> LENGTH: 1010
<212> TYPE: DNA
<213> ORGANISM: Artificial Sequence
<220> FEATURE:
<223> OTHER INFORMATION: Recombinant vector BiP:Leptin:M

<400> SEQUENCE: 10
tctagaggcg tgtgtgtgtg ttaaagaatg gctcgctcgt ttggagctaa cagtaccgtt    60
gtgttggcga tcatcttctt cggtgagtga ttttccgatc ttcttctccg atttagatct   120
cctctacatt gttgcttaat ctcagaacct tttttcgttg ttcctggatc tgaatgtgtt   180
tgtttgcaat tcacgatct taaaaggtta gatctcgatt ggtattgacg attggaatct    240
ttacgatttc aggatgttta tttgcgttgt cctctgcaat agaagaggct acgaagttaa   300

| | |
|---|---|
| ggatccaaga tgatgatgat aaggtgccta tccagaaagt ccaggatggc accaaagccc | 360 |
| tcatcaagac cattgtcacc aggatcaatg acatttcaca cacgcagtcg gtatccgcca | 420 |
| agcagagggt cactggcttg gacttcattc ctgggcttca ccccattctg agtttgtcca | 480 |
| agatggacca gactctggca gtctatcaac aggtcctcac cagcctgcct tcccaaaatg | 540 |
| tgctgcagat agccaatgac ctggagaatc tccgagacct cctccatctg ctggccttct | 600 |
| ccaagagctg ctccctgcct cagaccagtg gcctgcagaa gccagagagc ctggatggcg | 660 |
| tcctggaagc ctcactctac tccacagagg tggtggcttt gagcaggctg cagggctctc | 720 |
| tgcaggacat tcttcaacag ttggatgtta gccctgaatg ccgtgtcagg cgaactagtg | 780 |
| caaacatcac tgtggattac ttatataaca aggaaactaa attatttaca gcaaagctaa | 840 |
| atgttaatga gaatgtggaa tgtggaaaca atacttgcac aaacaatgag gtgcataacc | 900 |
| ttacagaatg taaaaatgcg tctgtttcca tatctcataa ttcatgtact gctcctgatt | 960 |
| acccatacga tgttccagat tacgcttccc acgatgagct ctagctcgag | 1010 |

```
<210> SEQ ID NO 11
<211> LENGTH: 174
<212> TYPE: DNA
<213> ORGANISM: Artificial Sequence
<220> FEATURE:
<223> OTHER INFORMATION: Aprotinin coding nucleic acid sequence

<400> SEQUENCE: 11
```

| | |
|---|---|
| cgaccggact tctgtcttga acctccttac acaggtcctt gcaaagctag aattatcagg | 60 |
| tatttttaca atgctaaggc aggactttgt caaacttttg tttacggggg atgtagagcg | 120 |
| aaacgtaaca atttcaagtc tgcagaggat tgtatgagaa cctgcggcgg tgcc | 174 |

```
<210> SEQ ID NO 12
<211> LENGTH: 261
<212> TYPE: DNA
<213> ORGANISM: Artificial Sequence
<220> FEATURE:
<223> OTHER INFORMATION: Cab transit peptide coding nucleic acid
      sequence

<400> SEQUENCE: 12
```

| | |
|---|---|
| atggcgtcga actcgcttat gagctgtggc atagccgccg tgtacccttc gcttctctct | 60 |
| tcttccaagt ctaaattcgt atccgccgga gttccactcc caaacgccgg gaatgttggt | 120 |
| cgtatcagaa tggctgctca ctggatgcct ggcgagccac gaccagctta ccttgacggt | 180 |
| tctgctcctg gtgactttgg gtttgaccca cttggacttg gagaagttcc agcgaacctt | 240 |
| gagagataca aagagtcaga g | 261 |

```
<210> SEQ ID NO 13
<211> LENGTH: 231
<212> TYPE: DNA
<213> ORGANISM: Artificial Sequence
<220> FEATURE:
<223> OTHER INFORMATION: F1-ATPase gamma subunit presequence coding
      nucleic acid sequence

<400> SEQUENCE: 13
```

| | |
|---|---|
| atggcaatgg ctgttttccg tcgcgaaggg aggcgtctcc tcccttcaat cgccgctcgc | 60 |
| ccaatcgctg ctatccgatc tcctctctct tctgaccagg aggaaggact tcttggagtt | 120 |
| cgatctatct caactcaagt ggtgcgtaac cgcatgaaga gtgttaagaa catccaaaag | 180 |
| atcacaaagg caatgaagat ggttgctgct tccaagctta gagcagttca g | 231 |

<210> SEQ ID NO 14
<211> LENGTH: 480
<212> TYPE: DNA
<213> ORGANISM: Artificial Sequence
<220> FEATURE:
<223> OTHER INFORMATION: G-domain coding nucleic acid sequence

<400> SEQUENCE: 14

```
gggggcaact ggacatgtgt gaaaggtgaa ccagtggtct acacgggggg gctagtaaaa      60
caatgcagat ggtgtggctt tgacttcaat gagcctgacg gactcccaca ctaccccata     120
ggtaagtgca ttttggcaaa tgagacaggt tacagaatag tggattcaac agactgtaac     180
agagatggtg ttgtaatcag cacagagggg agtcatgagt gcttgatcgg taacacgact     240
gtcaaggtgc atgcatcaga tgaaagactg ggcccatgc catgcagacc taaagagatc      300
gtctctagtg caggacctgt aaggaaaact tcctgtacat tcaactacgc aaaaactttg     360
aagaacaagt actatgagcc cagggacagc tacttccagc aatatatgct taagggcgag     420
tatcagtact ggtttgacct ggacgtgact gaccgccact cagattactt cgcagaagga     480
```

<210> SEQ ID NO 15
<211> LENGTH: 714
<212> TYPE: DNA
<213> ORGANISM: Artificial Sequence
<220> FEATURE:
<223> OTHER INFORMATION: GFP coding nucleic acid sequence

<400> SEQUENCE: 15

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccacct tcacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg      660
ctggagttcg tgaccgccgc cgggatcact ctcggcatgg acgagctgta caag           714
```

<210> SEQ ID NO 16
<211> LENGTH: 543
<212> TYPE: DNA
<213> ORGANISM: Artificial Sequence
<220> FEATURE:
<223> OTHER INFORMATION: LIF coding nucleic acid sequence

<400> SEQUENCE: 16

```
atgagccccc tccccatcac ccctgtcaac gccacctgtg ccatacgcca cccatgtcac      60
aacaacctca tgaaccagat caggagccaa ctggcacagc tcaatggcag tgccaatgcc     120
ctctttattc tctattacac agcccagggg gagccgttcc ccaacaacct ggacaagcta     180
tgtggcccca acgtgacgga cttccgcgcc ttccacgcca cggcacggaa gaaggccaag     240
```

```
ctggtggagc tgtaccgcat agtcgtgtac cttggcacct ccctgggcaa catcacccgc    300
gaccagaaga tcctcaaccc cagtgccctc agcctccaca gcaagctcaa cgccaccgcc    360
gacatcctgc gaggcctcct tagcaacgtg ctgtgccgcc tgtgcagcaa gtaccacgtg    420
ggccatgtgg acgtgaccta cggccctgac acctcgggta aggatgtctt ccagaagaag    480
aagctgggct gtcaactcct ggggaagtat aagcagatca tcgccgtgtt ggcccaggcc    540
ttc                                                                   543
```

<210> SEQ ID NO 17
<211> LENGTH: 181
<212> TYPE: PRT
<213> ORGANISM: Artificial Sequence
<220> FEATURE:
<223> OTHER INFORMATION: LIF

<400> SEQUENCE: 17

```
Met Ser Pro Leu Pro Ile Thr Pro Val Asn Ala Thr Cys Ala Ile Arg
1               5                   10                  15

His Pro Cys His Asn Asn Leu Met Asn Gln Ile Arg Ser Gln Leu Ala
            20                  25                  30

Gln Leu Asn Gly Ser Ala Asn Ala Leu Phe Ile Leu Tyr Tyr Thr Ala
        35                  40                  45

Gln Gly Glu Pro Phe Pro Asn Asn Leu Asp Lys Leu Cys Gly Pro Asn
    50                  55                  60

Val Thr Asp Phe Pro Pro Phe His Ala Asn Gly Thr Glu Lys Ala Lys
65                  70                  75                  80

Leu Val Glu Leu Tyr Arg Ile Val Val Tyr Leu Gly Thr Ser Leu Gly
                85                  90                  95

Asn Ile Thr Arg Asp Gln Lys Ile Leu Asn Pro Ser Ala Leu Ser Leu
            100                 105                 110

His Ser Lys Leu Asn Ala Thr Ala Asp Ile Leu Arg Gly Leu Leu Ser
        115                 120                 125

Asn Val Leu Cys Arg Leu Cys Ser Lys Tyr His Val Gly His Val Asp
    130                 135                 140

Val Thr Tyr Gly Pro Asp Thr Ser Gly Lys Asp Val Phe Gln Lys Lys
145                 150                 155                 160

Lys Leu Gly Cys Gln Leu Leu Gly Lys Tyr Lys Gln Ile Ile Ala Val
                165                 170                 175

Leu Ala Gln Ala Phe
            180
```

<210> SEQ ID NO 18
<211> LENGTH: 47
<212> TYPE: DNA
<213> ORGANISM: Artificial Sequence
<220> FEATURE:
<223> OTHER INFORMATION: BamHI-Ek-leptin-F primer

<400> SEQUENCE: 18

```
ggatccaaga tgatgatgat aaggtgccta tccagaaagt ccaggat            47
```

<210> SEQ ID NO 19
<211> LENGTH: 42
<212> TYPE: DNA
<213> ORGANISM: Artificial Sequence
<220> FEATURE:
<223> OTHER INFORMATION: leptin-furin-SpeI-R primer

<400> SEQUENCE: 19

```
actagttcgc ctgacacggc attcagggct aacatccaac tg                          42
```

<210> SEQ ID NO 20
<211> LENGTH: 24
<212> TYPE: DNA
<213> ORGANISM: Artificial Sequence
<220> FEATURE:
<223> OTHER INFORMATION: hspt-R primer

<400> SEQUENCE: 20

```
gaattcctta tctttaatca tatt                                              24
```

<210> SEQ ID NO 21
<211> LENGTH: 100
<212> TYPE: DNA
<213> ORGANISM: Artificial Sequence
<220> FEATURE:
<223> OTHER INFORMATION: M-3-HA-HDEL-F primer

<400> SEQUENCE: 21

```
tcataattca tgtactgctc ctgattaccc atacgatgtt ccagattacg cttcccacga       60
tgagctctag ctcgagatat gaagatgaag atgaaatatt                            100
```

<210> SEQ ID NO 22
<211> LENGTH: 100
<212> TYPE: DNA
<213> ORGANISM: Artificial Sequence
<220> FEATURE:
<223> OTHER INFORMATION: M-2-F primer

<400> SEQUENCE: 22

```
aatgtggaaa caatacttgc acaaacaatg aggtgcataa ccttacagaa tgtaaaaatg       60
cgtctgtttc catatctcat aattcatgta ctgctcctga                            100
```

<210> SEQ ID NO 23
<211> LENGTH: 109
<212> TYPE: DNA
<213> ORGANISM: Artificial Sequence
<220> FEATURE:
<223> OTHER INFORMATION: SpeI-M-1-F primer

<400> SEQUENCE: 23

```
actagtgcaa acatcactgt ggattactta tataacaagg aaactaaatt atttacagca       60
aagctaaatg ttaatgagaa tgtggaatgt ggaaacaata cttgcacaa                  109
```

<210> SEQ ID NO 24
<211> LENGTH: 30
<212> TYPE: DNA
<213> ORGANISM: Artificial Sequence
<220> FEATURE:
<223> OTHER INFORMATION: SpeI-HA-F primer

<400> SEQUENCE: 24

```
actagttacc catacgatgt tccagattac                                        30
```

<210> SEQ ID NO 25
<211> LENGTH: 30
<212> TYPE: DNA
<213> ORGANISM: Artificial Sequence
<220> FEATURE:
<223> OTHER INFORMATION: XbaI-Cab-F primer

<400> SEQUENCE: 25

```
tctagaatgg cgtcgaactc gcttatgagc                                    30

<210> SEQ ID NO 26
<211> LENGTH: 22
<212> TYPE: DNA
<213> ORGANISM: Artificial Sequence
<220> FEATURE:
<223> OTHER INFORMATION: Cab-BamHI-R primer

<400> SEQUENCE: 26
ggatcctctc tgactctttg ta                                            22

<210> SEQ ID NO 27
<211> LENGTH: 30
<212> TYPE: DNA
<213> ORGANISM: Artificial Sequence
<220> FEATURE:
<223> OTHER INFORMATION: XbaI-F1-F primer

<400> SEQUENCE: 27
tctagaatgg caatggctgt tttccgtcgc                                    30

<210> SEQ ID NO 28
<211> LENGTH: 30
<212> TYPE: DNA
<213> ORGANISM: Artificial Sequence
<220> FEATURE:
<223> OTHER INFORMATION: F1-BamHI-R primer

<400> SEQUENCE: 28
ggatcctctg aactgctcta agcttggaag                                    30

<210> SEQ ID NO 29
<211> LENGTH: 24
<212> TYPE: DNA
<213> ORGANISM: Artificial Sequence
<220> FEATURE:
<223> OTHER INFORMATION: SpeI-M-F primer

<400> SEQUENCE: 29
actagtgcaa acatcactgt ggat                                          24

<210> SEQ ID NO 30
<211> LENGTH: 24
<212> TYPE: DNA
<213> ORGANISM: Artificial Sequence
<220> FEATURE:
<223> OTHER INFORMATION: SpeI-M-N2Q-F primer

<400> SEQUENCE: 30
actagtgcac aaatcactgt ggat                                          24

<210> SEQ ID NO 31
<211> LENGTH: 27
<212> TYPE: DNA
<213> ORGANISM: Artificial Sequence
<220> FEATURE:
<223> OTHER INFORMATION: M-N30Q-F primer

<400> SEQUENCE: 31
gtggaatgtg gacaaaatac ttgcaca                                       27

<210> SEQ ID NO 32
<211> LENGTH: 27
<212> TYPE: DNA
<213> ORGANISM: Artificial Sequence
```

```
<220> FEATURE:
<223> OTHER INFORMATION: M-N30Q-R primer

<400> SEQUENCE: 32
tgtgcaagta ttttgtccac attccac                                              27

<210> SEQ ID NO 33
<211> LENGTH: 27
<212> TYPE: DNA
<213> ORGANISM: Artificial Sequence
<220> FEATURE:
<223> OTHER INFORMATION: M-N40Q-F primer

<400> SEQUENCE: 33
aatgaggtgc atcaacttac agaatgt                                              27

<210> SEQ ID NO 34
<211> LENGTH: 27
<212> TYPE: DNA
<213> ORGANISM: Artificial Sequence
<220> FEATURE:
<223> OTHER INFORMATION: M-N40Q-R primer

<400> SEQUENCE: 34
acattctgta agttgatgca cctcatt                                              27

<210> SEQ ID NO 35
<211> LENGTH: 27
<212> TYPE: DNA
<213> ORGANISM: Artificial Sequence
<220> FEATURE:
<223> OTHER INFORMATION: M-N46Q-F

<400> SEQUENCE: 35
acagaatgta aacaagcgtc tgtttcc                                              27

<210> SEQ ID NO 36
<211> LENGTH: 27
<212> TYPE: DNA
<213> ORGANISM: Artificial Sequence
<220> FEATURE:
<223> OTHER INFORMATION: M-N46Q-R primer

<400> SEQUENCE: 36
ggaaacagac gcttgtttac attctgt                                              27

<210> SEQ ID NO 37
<211> LENGTH: 51
<212> TYPE: DNA
<213> ORGANISM: Artificial Sequence
<220> FEATURE:
<223> OTHER INFORMATION: M-N40,46Q-F primer

<400> SEQUENCE: 37
aacaatgagg tgcatcaact tacagaatgt aaacaagcgt ctgtttccat a                   51

<210> SEQ ID NO 38
<211> LENGTH: 51
<212> TYPE: DNA
<213> ORGANISM: Artificial Sequence
<220> FEATURE:
<223> OTHER INFORMATION: M-N40,46Q-R primer

<400> SEQUENCE: 38
tatggaaaca gacgcttgtt tacattctgt aagttgatgc acctcattgt t                   51
```

<210> SEQ ID NO 39
<211> LENGTH: 35
<212> TYPE: DNA
<213> ORGANISM: Artificial Sequence
<220> FEATURE:
<223> OTHER INFORMATION: BamHI-M-F primer

<400> SEQUENCE: 39
ggatcccgat ggcaaacatc actgtggatt actta                          35

<210> SEQ ID NO 40
<211> LENGTH: 56
<212> TYPE: DNA
<213> ORGANISM: Artificial Sequence
<220> FEATURE:
<223> OTHER INFORMATION: M-GS2-SpeI-R primer

<400> SEQUENCE: 40
actagttgat ccaccaccag acccacctcc accatcagga gcagtacatg aattat    56

<210> SEQ ID NO 41
<211> LENGTH: 32
<212> TYPE: DNA
<213> ORGANISM: Artificial Sequence
<220> FEATURE:
<223> OTHER INFORMATION: BamHI-Ek-Apro primer

<400> SEQUENCE: 41
ggatcccgga tgacgacgat aagcgaccgg ac                             32

<210> SEQ ID NO 42
<211> LENGTH: 32
<212> TYPE: DNA
<213> ORGANISM: Artificial Sequence
<220> FEATURE:
<223> OTHER INFORMATION: BamHI-ek-Apr-F primer

<400> SEQUENCE: 42
ggatccaaga tgatgatgat aagcgaccgg ac                             32

<210> SEQ ID NO 43
<211> LENGTH: 42
<212> TYPE: DNA
<213> ORGANISM: Artificial Sequence
<220> FEATURE:
<223> OTHER INFORMATION: Apr-fu-SpeI-R primer

<400> SEQUENCE: 43
actagttcgc ctgacacggg caccgccgca ggttctcata ca                  42

<210> SEQ ID NO 44
<211> LENGTH: 45
<212> TYPE: DNA
<213> ORGANISM: Artificial Sequence
<220> FEATURE:
<223> OTHER INFORMATION: GFP-HDEL-stop-XhoI-R primer

<400> SEQUENCE: 44
ctcgagctag agctcatcgt gcttgtacag ctcgtccatg ccgag               45

<210> SEQ ID NO 45
<211> LENGTH: 42
<212> TYPE: DNA
<213> ORGANISM: Artificial Sequence
<220> FEATURE:
<223> OTHER INFORMATION: GFP-fu-SpeI-R primer

<400> SEQUENCE: 45
actagttcgc ctgacacgct tgtacagctc gtccatgccg ag          42

<210> SEQ ID NO 46
<211> LENGTH: 29
<212> TYPE: DNA
<213> ORGANISM: Artificial Sequence
<220> FEATURE:
<223> OTHER INFORMATION: SpeI-ek-GFP-F primer

<400> SEQUENCE: 46
actagtgatg acgacgatag gtgagcaag          29

<210> SEQ ID NO 47
<211> LENGTH: 22
<212> TYPE: DNA
<213> ORGANISM: Artificial Sequence
<220> FEATURE:
<223> OTHER INFORMATION: AtACT2-5 primer

<400> SEQUENCE: 47
tatgaattac ccgatgggca ag          22

<210> SEQ ID NO 48
<211> LENGTH: 21
<212> TYPE: DNA
<213> ORGANISM: Artificial Sequence
<220> FEATURE:
<223> OTHER INFORMATION: AtACT2-3 primer

<400> SEQUENCE: 48
tggaacaaga cttctgggca t          21

<210> SEQ ID NO 49
<211> LENGTH: 37
<212> TYPE: DNA
<213> ORGANISM: Artificial Sequence
<220> FEATURE:
<223> OTHER INFORMATION: leptin- F-qRT1-F primer

<400> SEQUENCE: 49
tcggtatccg ccaagcagtg cctatccaga aagtcca          37

<210> SEQ ID NO 50
<211> LENGTH: 40
<212> TYPE: DNA
<213> ORGANISM: Artificial Sequence
<220> FEATURE:
<223> OTHER INFORMATION: leptin- R-qRT1-R primer

<400> SEQUENCE: 50
ggtgaagccc aggaatgaag gcattcaggg ctaacatcca          40

<210> SEQ ID NO 51
<211> LENGTH: 39
<212> TYPE: PRT
<213> ORGANISM: Artificial Sequence
<220> FEATURE:
<223> OTHER INFORMATION: Exendin-4

<400> SEQUENCE: 51

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser

```
                    20                  25                  30

Ser Gly Ala Pro Pro Ser
        35

<210> SEQ ID NO 52
<211> LENGTH: 30
<212> TYPE: PRT
<213> ORGANISM: Artificial Sequence
<220> FEATURE:
<223> OTHER INFORMATION: GLP-1

<400> SEQUENCE: 52

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 53
<211> LENGTH: 438
<212> TYPE: DNA
<213> ORGANISM: Artificial Sequence
<220> FEATURE:
<223> OTHER INFORMATION: Leptin coding nucleic acid sequence

<400> SEQUENCE: 53
gtgcctatcc agaaagtcca ggatggcacc aaagccctca tcaagaccat tgtcaccagg      60
atcaatgaca tttcacacac gcagtcggta tccgccaagc agagggtcac tggcttggac     120
ttcattcctg ggcttcaccc cattctgagt ttgtccaaga tggaccagac tctggcagtc     180
tatcaacagg tcctcaccag cctgccttcc caaaatgtgc tgcagatagc caatgacctg     240
gagaatctcc gagacctcct ccatctgctg gccttctcca agagctgctc cctgcctcag     300
accagtggcc tgcagaagcc agagagcctg gatggcgtcc tggaagcctc actctactcc     360
acagaggtgg tggctttgag caggctgcag ggctctctgc aggacattct tcaacagttg     420
gatgttagcc ctgaatgc                                                   438
```